United States Patent
Nettekoven et al.

(10) Patent No.: US 7,514,433 B2
(45) Date of Patent: Apr. 7, 2009

(54) 1H-INDOLE-6-YL-PIPERAZIN-1-YL-METHANONE DERIVATIVES

(75) Inventors: Matthias Nettekoven, Grenzach-Wyhlen (DE); Olivier Roche, Folgensbourg (FR)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 11/880,083

(22) Filed: Jul. 19, 2007

(65) Prior Publication Data

US 2008/0032976 A1 Feb. 7, 2008

(30) Foreign Application Priority Data

Aug. 3, 2006 (EP) .................. 06118419

(51) Int. Cl.
*A61K 31/5377* (2006.01)
*A61K 31/496* (2006.01)
*C07D 401/14* (2006.01)
*C07D 413/14* (2006.01)

(52) U.S. Cl. ............... 514/235.2; 514/253.09; 514/254.09; 544/121; 544/364; 544/373

(58) Field of Classification Search ............ 544/364, 544/373
See application file for complete search history.

(56) References Cited

U.S. PATENT DOCUMENTS

| | | | |
|---|---|---|---|
| 4,598,089 A | 7/1986 | Hadvary et al. | |
| 4,931,463 A | 6/1990 | Barbier et al. | |
| 4,983,746 A | 1/1991 | Barbier et al. | |
| 5,175,186 A | 12/1992 | Barbier et al. | |
| 5,246,960 A | 9/1993 | Barbier et al. | |
| 5,274,143 A | 12/1993 | Ramig et al. | |
| 5,399,720 A | 3/1995 | Karpf et al. | |
| 5,420,305 A | 5/1995 | Ramig et al. | |
| 6,004,996 A | 12/1999 | Shah et al. | |
| 6,380,201 B1 * | 4/2002 | Johnson et al. | 514/255.05 |
| 2005/0096330 A1 | 5/2005 | Boettcher et al. | |
| 2005/0282864 A1 | 12/2005 | McArthur et al. | |
| 2006/0084679 A1 | 4/2006 | McArthur et al. | |
| 2006/0160855 A1 | 7/2006 | Nettekoven et al. | |

FOREIGN PATENT DOCUMENTS

| | | |
|---|---|---|
| EP | 185 359 | 6/1986 |
| EP | 189 577 | 8/1986 |
| EP | 443 449 | 8/1991 |
| EP | 524 495 | 1/1993 |
| WO | WO 99/34786 | 7/1999 |
| WO | WO 00/09122 | 2/2000 |
| WO | WO 00/09123 | 2/2000 |
| WO | WO 2004/000831 A1 | 12/2003 |
| WO | WO 2004/035544 A1 | 4/2004 |
| WO | WO 2006/035308 A1 | 4/2006 |

OTHER PUBLICATIONS

Masaki et al., Endocrinol., 144, pp. 2741-2748 (2003).
Hancock et al., European J. of Pharmacol., 487, pp. 183-197 (2004).
Timmermann, H., J. Med. Chem., 33, pp. 4-11 (1990).

* cited by examiner

*Primary Examiner*—Emily Bernhardt
(74) *Attorney, Agent, or Firm*—George W. Johnston; Dennis P. Tramaloni; Brian C. Remy

(57) ABSTRACT

The present invention relates to the compounds of formula I:

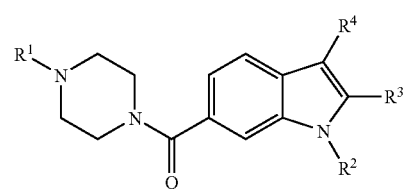

wherein $R^1$ to $R^4$ are as defined in the description and claims, and pharmaceutically acceptable salts thereof. The compounds are useful for the treatment and/or prevention of diseases which are associated with the modulation of H3 receptors.

17 Claims, No Drawings

1H-INDOLE-6-YL-PIPERAZIN-1-YL-METHANONE DERIVATIVES

PRIORITY TO RELATED APPLICATION(S)

This application claims the benefit of European Patent Application No. 06118419.8, filed Aug. 3, 2006, which is hereby incorporated by reference in its entirety.

BACKGROUND OF THE INVENTION

The present invention is concerned with novel 1H-indol-6-yl-piperazin-1-yl-methanone derivatives, their manufacture, pharmaceutical compositions containing them and their use to treat diseases such as obesity and other disorders which are modulated by histamine 3 receptor (H3) antagonists and/or inverse agonists.

Histamine (2-(4-imidazolyl)ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tubero-mammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2H3 and H4 receptors.

H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

It is therefore an object of the present invention to provide selective, directly acting H3 receptor antagonists respectively inverse agonists. Such antagonists/inverse agonists are useful as therapeutically active substances, particularly in the treatment and/or prevention of diseases which are associated with the modulation of H3 receptors.

SUMMARY OF THE INVENTION

The present invention relates to the compounds of the formula I including all pharmaceutically acceptable salts and esters thereof wherein formula I is:

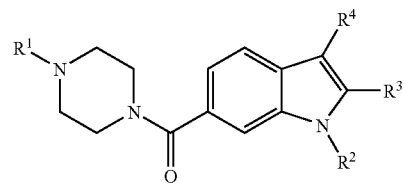

wherein $R^1$-$R^4$ are as defined in the detailed description and in the claims.

The compounds of formula I are antagonists and/or inverse agonists at the histamine 3 receptor (H3 receptor) and are useful in the treatment of diseases such as obesity and other diseases which are modulated by such by H3 receptor antagonists and/or inverse agonists.

DETAILED DESCRIPTION OF THE INVENTION

In the present description the term "alkyl", alone or in combination with other groups, refers to a branched or straight-chain monovalent saturated aliphatic hydrocarbon radical of one to twenty carbon atoms. In preferred embodiments the alkyl has one to sixteen carbon atoms and more preferably one to ten carbon atoms.

The term "lower alkyl" or "$C_1$-$C_7$-alkyl", alone or in combination, signifies a straight-chain or branched-chain alkyl group with 1 to 7 carbon atoms. In preferred embodiments the lower alkyl or $C_1$-$C_7$-alkyl is a straight or branched-chain alkyl group with 1 to 6 carbon atoms and particularly preferred a straight or branched-chain alkyl group with 1 to 4 carbon atoms. Examples of straight-chain and branched $C_1$-$C_7$ alkyl groups are methyl, ethyl, propyl, isopropyl, butyl, isobutyl, tert.-butyl, the isomeric pentyls, the isomeric hexyls and the isomeric heptyls, preferably methyl and ethyl and most preferably methyl.

The term "cycloalkyl" or "$C_3$-$C_7$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclobutyl and cyclopentyl.

The term "alkoxy" or "lower alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert.-butoxy, preferably methoxy and ethoxy and most preferably methoxy.

The term "lower alkoxyalkyl" or "($C_1$-$C_7$-alkoxy-$C_1$-$C_7$-alkyl" refers to lower alkyl groups as defined previously wherein at least one of the hydrogen atoms of the lower alkyl groups is replaced by an alkoxy group, preferably methoxy or ethoxy. Among the preferred lower alkoxyalkyl groups are 2-methoxyethyl and 3-methoxypropyl.

The term "halogen" refers to fluorine, chlorine, bromine or iodine. In preferred embodiments, the halogen is fluorine, chlorine, or bromine.

The term "lower halogenalkyl" or "halogen-$C_1$-$C_7$-alkyl" refers to lower alkyl groups as defined previously wherein at least one of the hydrogen atoms of the lower alkyl group is replaced by a halogen atom (preferably fluoro or chloro, and most preferably fluoro). Among the preferred halogenated lower alkyl groups are trifluoromethyl, difluoromethyl, trifluoroethyl, 2,2-difluoroethyl, fluoromethyl and chloromethyl, with trifluoromethyl or 2,2-difluoroethyl being especially preferred.

The term "lower halogenalkoxy" or "halogen-$C_1$-$C_7$-alkoxy" refers to lower alkoxy groups as defined previously wherein at least one of the hydrogen atoms of the lower alkoxy group is replaced by a halogen atom.

The term "lower phenylalkyl" or "phenyl-$C_{1-7}$-alkyl" refers to lower alkyl groups as defined previously wherein at least one of the hydrogen atoms of the lower alkyl group is replaced by a phenyl group. Preferred lower phenylalkyl groups are benzyl or phenethyl.

The term "heterocyclyl" refers to a saturated or partly unsaturated ring which can comprise one, two or three atoms selected from nitrogen, oxygen and/or sulphur. Examples of heterocyclyl rings include aziridinyl, azetidinyl, pyrrolidinyl, piperidinyl, tetrahydropyridyl, azepinyl, piperazinyl, pyrazolidinyl, imidazolinyl, imidazolidinyl, oxazolidinyl, isoxazolidinyl, morpholinyl, thiazolidinyl, isothiazolidinyl, thiadiazolylidinyl, dihydrofuryl, tetrahydrofuryl, oxiranyl, oxetanyl, dihydropyranyl, tetrahydropyranyl and thiomorpholinyl.

The term "N-heterocyclic ring" refers to a heterocyclyl containing at least one nitrogen atom. Examples of "N-heterocyclic rings" include aziridinyl, azetidinyl, pyrrolidinyl, piperidinyl, azepinyl, piperazinyl, morpholinyl and thiomorpholinyl, and also rings additionally containing a carbonyl group such as pyrrolidin-2-one or partly unsaturated rings such as tetrahydropyridyl. Preferred "N-heterocyclic rings" are pyrrolidinyl, piperidinyl, morpholinyl and 1,2,3,6-tetrahydropyridyl.

In reference to a particular group or molecule, the term "substituted" refers to the fact that at least one of the hydrogen atoms of that group or molecule is replaced by some other substituent.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compounds of formula I can also be present in the form of zwitterions. Particularly preferred pharmaceutically acceptable salts of the compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space and have one or more asymmetric carbon atoms are termed "stereoisomers". Stereoisomers that are not mirror images of one another are termed "diastereoisomers", and stereoisomers that are non-superimposable mirror images are termed "enantiomers", or sometimes optical isomers.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 100 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

In detail, the present invention relates to the compounds of formula I and all pharmaceutically acceptable salts thereof wherein formula I is:

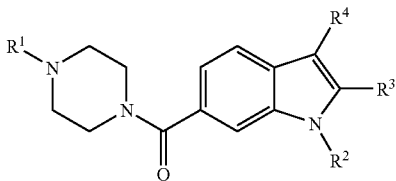

wherein:
(a) $R^1$ is lower alkyl or cycloalkyl;
(b) $R^2$ is selected from the group consisting of:
(1) hydrogen;
(2) lower alkyl;
(3) lower halogenalkyl;
(4) —$SO_2$—$R^5$, wherein $R^5$ is lower alkyl or phenyl optionally substituted by one or two substituents independently selected from the group consisting of lower alkyl, lower alkoxy, halogen, cyano, lower halogenalkyl and lower halogenalkoxy;
(5) —C(O)—$(CH_2)_n$-phenyl, wherein n is 0, 1 or 2 and wherein the phenyl ring is optionally substituted by one or two substituents independently selected from the group consisting of lower alkyl, lower alkoxy, halogen, cyano, lower halogenalkyl and lower halogenalkoxy;
(6) —$(CH_2)_n$-cycloalkyl, wherein n is 0, 1 or 2;
(7) pyridyl; and
(8) —$(CH_2)_n$-phenyl, wherein n is 0, 1 or 2 and wherein the phenyl ring is optionally substituted by one, two or three substituents independently selected from the group consisting of lower alkyl, lower halogenalkyl, halogen, cyano, lower alkoxy and lower halogenalkoxy;
(c) $R^3$ is hydrogen or lower alkyl; and
(d) $R^4$ is an N-heterocyclic ring selected from the group consisting of pyrrolidine, piperidine, 1,2,3,6-tetrahydropyridine, and morpholine; wherein the nitrogen atom of the N-heterocyclic ring is substituted by a group selected from the group consisting of:
(1) hydrogen;
(2) lower alkyl;
(3) cycloalkyl;
(4) lower cyanoalkyl;
(5) lower halogenalkyl;
(6) lower alkoxyalkyl;
(7) —$SO_2$—$R^6$, wherein $R^6$ is selected from the group consisting of:
(i) lower alkyl,
(ii) phenyl which is optionally substituted by one or two substituents selected from the group consisting of lower alkyl, lower alkoxy, halogen, cyano, lower halogenalkyl and lower halogenalkoxy,
(iii) thienyl, and
(iv) pyridyl;
(8) —C(O)—$R^7$, wherein $R^7$ is selected from the group consisting of:
(i) lower alkyl,
(ii) phenyl which is optionally substituted by one or two substituents selected from the group consisting of lower alkyl, lower alkoxy, halogen, cyano, lower halogenalkyl and lower halogenalkoxy,
(iii) thienyl, and
(iv) pyridyl;
(9) —C(O)—$NR^8R^9$, wherein $R^8$ and $R^9$ independently from each other are selected from the group consisting of:
(i) lower alkyl,
(ii) phenyl, and
(iii) lower phenylalkyl;
or alternatively, $R^8$ and $R^9$ together with the nitrogen atom to which they are attached to, form a heterocyclic ring selected from the group consisting of pyrrolidine, piperidine, piperazine and morpholine, and
(10) —$(CH_2)_p$-phenyl, wherein p is 0, 1 or 2 and wherein the phenyl ring is optionally substituted by one or two substituents selected from the group consisting of lower alkyl, lower alkoxy, halogen, cyano, lower halogenalkyl and lower halogenalkoxy.

Preferred are compounds of formula I according to the present invention, wherein $R^4$ is a N-heterocyclic ring selected from the group consisting of pyrrolidine, piperidine, 1,2,3,6-tetrahydropyridine and morpholine, wherein the nitrogen atom is substituted by a group selected from the group consisting of hydrogen, lower alkyl, cycloalkyl, lower cyanoalkyl, lower halogenalkyl and lower alkoxyalkyl. More preferably, the nitrogen atom is substituted by a group selected from the group consisting of lower alkyl, cycloalkyl, lower cyanoalkyl, lower halogenalkyl and lower alkoxyalkyl.

A preferred group of compounds of formula I according to the invention are furthermore those, wherein $R^4$ is a N-heterocyclic ring selected from pyrrolidine, piperidine, 1,2,3,6-tetrahydropyridine and morpholine, wherein the nitrogen atom is substituted by a group selected from the group consisting of:
—$SO_2$—$R^6$, wherein $R^6$ is selected from the group consisting of (i) lower alkyl, (ii) phenyl which is optionally substituted by one or two groups selected from the group consisting of lower alkyl, lower alkoxy, halogen, cyano, lower halogenalkyl and lower halogenalkoxy, (iii) thienyl, and (iv) pyridyl.
—C(O)—$R^7$, wherein $R^7$ is selected from the group consisting of (i) lower alkyl, (ii) phenyl optionally substituted by one or two groups selected from the group consisting of lower alkyl, lower alkoxy, halogen, cyano, lower halogenalkyl and lower halogenalkoxy, (iii) thienyl, and (iv) pyridyl;
—C(O)—$NR^8R^9$, wherein $R^8$ and $R^9$ independently from each other are selected from (i) lower alkyl, (ii) phenyl, and (iii) lower phenylalkyl; or alternatively, $R^8$ and $R^9$ together with the nitrogen atom to which they are attached to form a heterocyclic ring selected from the group consisting of pyrrolidine, piperidine, piperazine and morpholine, and
—$(CH_2)_p$-phenyl, wherein p is 0, 1 or 2 and wherein the phenyl ring is optionally substituted by one or two groups selected from the group consisting of lower alkyl, lower alkoxy, halogen, cyano, lower halogenalkyl and lower halogenalkoxy.

Especially preferred are the compounds of formula I according to the present invention, wherein $R^4$ is a N-heterocyclic ring selected from the group consisting of piperidine and 1,2,3,6-tetrahydropyridine.

Most preferably, $R^4$ is piperidin-4-yl, wherein the piperidin-4-yl group is optionally substituted as described herein before.

Also preferred are compounds of formula I according to the invention, wherein the N-heterocyclic ring is pyrrolidine.

Furthermore, compounds of formula I of the present invention are preferred, wherein the N-heterocyclic ring is morpholine.

Preferred are further compounds of formula I according to the present invention, wherein $R^1$ is lower alkyl, with those compounds of formula I, wherein $R^1$ is isopropyl or tert-butyl, being especially preferred.

Also preferred are compounds of formula I according to the present invention, wherein $R^1$ is cycloalkyl, with those compounds of formula I, wherein $R^1$ is cyclobutyl or cyclopentyl, being especially preferred.

Thus, compounds wherein $R^1$ is selected from the group consisting of isopropyl, tert-butyl, cyclobutyl and cyclopentyl, are especially preferred.

A group of preferred compounds of formula I according to the invention are those, wherein $R^2$ is hydrogen.

Furthermore, compounds of formula I according to the present invention are preferred, wherein $R^2$ is selected from the group consisting of:
(1) lower alkyl,
(2) lower halogenalkyl,
(3) —$SO_2$—$R^5$, wherein $R^5$ is lower alkyl or phenyl optionally substituted by one or two groups selected from the group consisting of lower alkyl, lower alkoxy, halogen, cyano, lower halogenalkyl and lower halogenalkoxy, (4) —C(O)—$(CH_2)_n$-phenyl, wherein the phenyl ring is optionally substituted by one or two groups selected from the group consisting of lower alkyl, lower alkoxy, halogen, cyano, lower halogenalkyl and lower halogenalkoxy, (5) —$(CH_2)_n$-cycloalkyl, (6) pyridyl, and (7) —$(CH_2)_n$-phenyl, wherein the phenyl ring is optionally substituted by one, two or three groups independently selected from the group consisting of lower alkyl, lower halogenalkyl, halogen, cyano, lower alkoxy and lower halogenalkoxy; and wherein n is 0, 1 or 2.

Within this group, the compounds of formula I are preferred, wherein $R^2$ is lower alkyl.

Also especially preferred are the compounds of formula I according to the invention, wherein $R^2$ is —$(CH_2)_n$-phenyl, wherein the phenyl ring is optionally substituted by one, two or three groups independently selected from the group consisting of lower alkyl, lower halogenalkyl, halogen, cyano, lower alkoxy and lower halogenalkoxy; and wherein n is 0, 1 or 2.

Most preferably, the integer n is 0.

$R^3$ is hydrogen or lower alkyl. Preferably, $R^3$ is hydrogen or methyl.

More preferred are compounds of formula I according to the invention, wherein $R^3$ is hydrogen.

Preferred compounds of formula I of the present invention are the following:

[3-(1-isobutyl-1,2,3,6-tetrahydro-pyridin-4-yl)-1H-indol-6-yl]-(4-isopropyl-piperazin-1-yl)-methanone; hydrochloride,

[3-(1-isobutyl-piperidin-4-yl)-1H-indol-6-yl]-(4-isopropyl-piperazin-1-yl)-methanone; hydrochloride, (4-isopropyl-piperazin-1-yl)-[3-(1-isopropyl-piperidin-4-yl)-1H-indol-6-yl]-methanone; hydrochloride,

[3-(1-benzyl-1,2,3,6-tetrahydro-pyridin-4-yl)-1H-indol-6-yl]-(4-isopropyl-piperazin-1-yl)-methanone,

[3-(1-benzyl-1,2,3,6-tetrahydro-pyridin-4-yl)-1H-indol-6-yl]-(4-cyclopentyl-piperazin-1-yl)-methanone, (4-isopropyl-piperazin-1-yl)-[3-(1-methyl-piperidin-4-yl)-1H-indol-6-yl]-methanone, (4-isopropyl-piperazin-1-yl)-(3-piperidin-4-yl-1H-indol-6-yl)-methanone; hydrochloride, (4-cyclopentyl-piperazin-1-yl)-(3-piperidin-4-yl-1H-indol-6-yl)-methanone, (4-isopropyl-piperazin-1-yl)-(3-piperidin-3-yl-1H-indol-6-yl)-methanone, (4-isopropyl-piperazin-1-yl)-[3-(1-isopropyl-piperidin-3-yl)-1H-indol-6-yl]-methanone,

[3-(1-cyclopentyl-piperidin-3-yl)-1H-indol-6-yl]-(4-isopropyl-piperazin-1-yl)-methanone, (4-cyclopentyl-piperazin-1-yl)-[3-(1-isopropyl-piperidin-4-yl)-1H-indol-6-yl]-methanone,

[3-(1-cyclopentyl-piperidin-4-yl)-1H-indol-6-yl]-(4-isopropyl-piperazin-1-yl)-methanone, (4-cyclopentyl-piperazin-1-yl)-[3-(1-cyclopentyl-piperidin-4-yl)-1H-indol-6-yl]-methanone,

[3-(1-cyclobutyl-piperidin-4-yl)-1H-indol-6-yl]-(4-isopropyl-piperazin-1-yl)-methanone,

[3-(1-cyclobutyl-piperidin-4-yl)-1H-indol-6-yl]-(4-cyclopentyl-piperazin-1-yl)-methanone,

[3-(1-cyclobutyl-piperidin-3-yl)-1H-indol-6-yl]-(4-isopropyl-piperazin-1-yl)-methanone,

[3-(1-ethyl-piperidin-4-yl)-1H-indol-6-yl]-(4-isopropyl-piperazin-1-yl)-methanone, (4-isopropyl-piperazin-1-yl)-[3-(1-propyl-piperidin-4-yl)-1H-indol-6-yl]-methanone, {4-[6-(4-isopropyl-piperazine-1-carbonyl)-1H-indol-3-yl]-piperidin-1-yl}-acetonitrile, {3-[1-(2,2-difluoro-ethyl)-piperidin-4-yl]-1H-indol-6-yl}-(4-isopropyl-piperazin-1-yl)-methanone, (4-isopropyl-piperazin-1-yl)-{3-[1-(2-methoxy-ethyl)-piperidin-4-yl]-1H-indol-6-yl}-methanone, (4-cyclopentyl-piperazin-1-yl)-[3-(1-propyl-piperidin-4-yl)-1H-indol-6-yl]-methanone, (4-cyclopentyl-piperazin-1-yl)-[3-(1-isobutyl-piperidin-4-yl)-1H-indol-6-yl]-methanone, (4-cyclopentyl-piperazin-1-yl)-{3-[1-(2,2-difluoro-ethyl)-piperidin-4-yl]-1H-indol-6-yl}-methanone, (4-cyclopentyl-piperazin-1-yl)-{3-[1-(2-methoxy-ethyl)-piperidin-4-yl]-1H-indol-6-yl}-methanone, (4-isopropyl-piperazin-1-yl)-[3-(1-propyl-piperidin-3-yl)-1H-indol-6-yl]-methanone,

[3-(1-isobutyl-piperidin-3-yl)-1H-indol-6-yl]-(4-isopropyl-piperazin-1-yl)-methanone, (4-isopropyl-piperazin-1-yl)-{3-[1-(2-methoxy-ethyl)-piperidin-3-yl]-1H-indol-6-yl}-methanone, 4-[6-(4-isopropyl-piperazine-1-carbonyl)-1H-indol-3-yl]-piperidine-1-carboxylic acid diethylamide,

[3-(1-benzyl-piperidin-4-yl)-1H-indol-6-yl]-(4-isopropyl-piperazin-1-yl)-methanone, 1-{4-[6-(4-isopropyl-piperazine-1-carbonyl)-1H-indol-3-yl]-piperidin-1-yl}-ethanone, (4-isopropyl-piperazin-1-yl)-[3-(1-methanesulfonyl-piperidin-4-yl)-1H-indol-6-yl]-methanone,

[1-ethyl-3-(1-isobutyl-1,2,3,6-tetrahydro-pyridin-4-yl)-1H-indol-6-yl]-(4-isopropyl-piperazin-1-yl)-methanone; hydrochloride, (4-cyclopentyl-piperazin-1-yl)-[3-(1-methyl-pyrrolidin-2-yl)-1H-indol-6-yl]-methanone, (4-isopropyl-piperazin-1-yl)-[3-(1-methyl-pyrrolidin-2-yl)-1H-indol-6-yl]-methanone,

[3-(1-benzyl-pyrrolidin-2-yl)-1H-indol-6-yl]-(4-isopropyl-piperazin-1-yl)-methanone,

[3-(1-benzyl-pyrrolidin-2-yl)-1H-indol-6-yl]-(4-cyclopentyl-piperazin-1-yl)-methanone, (4-isopropyl-piperazin-1-yl)-{3-[1-(4-methoxy-phenyl)-1,2,3,6-tetrahydro-pyridin-4-yl]-1H-indol-6-yl}-methanone, (4-isopropyl-piperazin-1-yl)-{3-[1-(4-methoxy-phenyl)-piperidin-4-yl]-1H-indol-6-yl}-methanone; hydrochloride, (4-cyclopentyl-piperazin-1-yl)-{3-[1-(4-methoxy-phenyl)-piperidin-4-yl]-1H-indol-6-yl}-methanone; hydrochloride,

[3-(1-isobutyl-1,2,3,6-tetrahydro-pyridin-4-yl)-1-methyl-1H-indol-6-yl]-(4-isopropyl-piperazin-1-yl)-methanone; hydrochloride,
[3-(1-isobutyl-1,2,3,6-tetrahydro-pyridin-4-yl)-1-isopropyl-1H-indol-6-yl]-(4-isopropyl-piperazin-1-yl)-methanone; hydrochloride,
[3-(1-isobutyl-1,2,3,6-tetrahydro-pyridin-4-yl)-1-methanesulfonyl-1H-indol-6-yl]-(4-isopropyl-piperazin-1-yl)-methanone,
[3-(1-isobutyl-piperidin-4-yl)-1-methyl-1H-indol-6-yl]-(4-isopropyl-piperazin-1-yl)-methanone; hydrochloride,
[1-ethyl-3-(1-isobutyl-piperidin-4-yl)-1H-indol-6-yl]-(4-isopropyl-piperazin-1-yl)-methanone; hydrochloride,
[3-(1-isobutyl-piperidin-4-yl)-1-isopropyl-1H-indol-6-yl]-(4-isopropyl-piperazin-1-yl)-methanone; hydrochloride,
[1-(2,2-difluoro-ethyl)-3-(1-isobutyl-piperidin-4-yl)-1H-indol-6-yl]-(4-isopropyl-piperazin-1-yl)-methanone,
[1-isobutyl-3-(1-isobutyl-piperidin-4-yl)-1H-indol-6-yl]-(4-isopropyl-piperazin-1-yl)-methanone,
[3-(1-isobutyl-piperidin-4-yl)-1-methanesulfonyl-1H-indol-6-yl]-(4-isopropyl-piperazin-1-yl)-methanone,
4-[3-(1-isobutyl-1,2,3,6-tetrahydro-pyridin-4-yl)-6-(4-isopropyl-piperazine-1-carbonyl)-indol-1-yl]-benzonitrile,
[3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone,
[3-(1-isobutyl-1,2,3,6-tetrahydro-pyridin-4-yl)-1-(4-methoxy-phenyl)-1H-indol-6-yl]-(4-isopropyl-piperazin-1-yl)-methanone,
[1-(2,4-difluoro-phenyl)-3-(1-isobutyl-1,2,3,6-tetrahydro-pyridin-4-yl)-1H-indol-6-yl]-(4-isopropyl-piperazin-1-yl)-methanone,
[1-(4-fluoro-phenyl)-3-(1-isobutyl-1,2,3,6-tetrahydro-pyridin-4-yl)-1H-indol-6-yl]-(4-isopropyl-piperazin-1-yl)-methanone,
[3-(1-isobutyl-1,2,3,6-tetrahydro-pyridin-4-yl)-1-pyridin-3-yl-1H-indol-6-yl]-(4-isopropyl-piperazin-1-yl)-methanone,
[1-(3-chloro-4-methyl-phenyl)-3-(1-isobutyl-1,2,3,6-tetrahydro-pyridin-4-yl)-1H-indol-6-yl]-(4-isopropyl-piperazin-1-yl)-methanone,
[1-(5-fluoro-2-methyl-phenyl)-3-(1-isobutyl-1,2,3,6-tetrahydro-pyridin-4-yl)-1H-indol-6-yl]-(4-isopropyl-piperazin-1-yl)-methanone,
[3-(1-isobutyl-1,2,3,6-tetrahydro-pyridin-4-yl)-1-p-tolyl-1H-indol-6-yl]-(4-isopropyl-piperazin-1-yl)-methanone,
3-[3-(1-isobutyl-1,2,3,6-tetrahydro-pyridin-4-yl)-6-(4-isopropyl-piperazine-1-carbonyl)-indol-1-yl]-benzonitrile,
[3-(1-isobutyl-piperidin-4-yl)-1-(4-trifluoromethyl-phenyl)-1H-indol-6-yl]-(4-isopropyl-piperazin-1-yl)-methanone,
[3-(1-isobutyl-piperidin-4-yl)-1-(4-methoxy-phenyl)-1H-indol-6-yl]-(4-isopropyl-piperazin-1-yl)-methanone,
[1-(2,4-difluoro-phenyl)-3-(1-isobutyl-piperidin-4-yl)-1H-indol-6-yl]-(4-isopropyl-piperazin-1-yl)-methanone,
4-[3-(1-isobutyl-piperidin-4-yl)-6-(4-isopropyl-piperazine-1-carbonyl)-indol-1-yl]-benzonitrile,
[3-(1-isobutyl-piperidin-4-yl)-1-(3-trifluoromethyl-phenyl)-1H-indol-6-yl]-(4-isopropyl-piperazin-1-yl)-methanone,
[1-(4-fluoro-phenyl)-3-(1-isobutyl-piperidin-4-yl)-1H-indol-6-yl]-(4-isopropyl-piperazin-1-yl)-methanone,
[3-(1-isobutyl-piperidin-4-yl)-1-pyridin-3-yl-1H-indol-6-yl]-(4-isopropyl-piperazin-1-yl)-methanone,
[1-(3-chloro-4-methyl-phenyl)-3-(1-isobutyl-piperidin-4-yl)-1H-indol-6-yl]-(4-isopropyl-piperazin-1-yl)-methanone,
[3-(1-isobutyl-piperidin-4-yl)-1-p-tolyl-1H-indol-6-yl]-(4-isopropyl-piperazin-1-yl)-methanone,
3-[3-(1-isobutyl-piperidin-4-yl)-6-(4-isopropyl-piperazine-1-carbonyl)-indol-1-yl]-benzonitrile,
[3-(1-isobutyl-piperidin-4-yl)-1-(4-trifluoromethoxy-phenyl)-1H-indol-6-yl]-(4-isopropyl-piperazin-1-yl)-methanone,
(4-isopropyl-piperazin-1-yl)-(3-piperidin-2-yl-1H-indol-6-yl)-methanone,
(4-isopropyl-piperazin-1-yl)-[3-(1-isopropyl-piperidin-2-yl)-1H-indol-6-yl]-methanone,
[3-(1-isobutyl-piperidin-2-yl)-1H-indol-6-yl]-(4-isopropyl-piperazin-1-yl)-methanone,
4-[6-(4-isopropyl-piperazine-1-carbonyl)-3-piperidin-3-yl-indol-1-yl]-benzonitrile,
4-{3-[6-(4-isopropyl-piperazine-1-carbonyl)-1H-indol-3-yl]-piperidin-1-yl}-benzonitrile,
{3-[1-(3,5-difluoro-benzoyl)-piperidin-3-yl]-1H-indol-6-yl}-(4-isopropyl-piperazin-1-yl)-methanone,
(4-isopropyl-piperazin-1-yl)-{3-[1-(thiophene-3-carbonyl)-piperidin-3-yl]-1H-indol-6-yl}-methanone,
3-{3-[6-(4-isopropyl-piperazine-1-carbonyl)-1H-indol-3-yl]-piperidine-1-carbonyl}-benzonitrile,
{3-[1-(5-fluoro-2-methyl-benzoyl)-piperidin-3-yl]-1H-indol-6-yl}-(4-isopropyl-piperazin-1-yl)-methanone,
{3-[1-(3,4-difluoro-benzoyl)-piperidin-3-yl]-1H-indol-6-yl}-(4-isopropyl-piperazin-1-yl)-methanone,
4-{3-[6-(4-isopropyl-piperazine-1-carbonyl)-1H-indol-3-yl]-piperidine-1-carbonyl}-benzonitrile,
{3-[1-(3,4-dichloro-benzoyl)-piperidin-3-yl]-1H-indol-6-yl}-(4-isopropyl-piperazin-1-yl)-methanone,
(4-isopropyl-piperazin-1-yl)-{3-[1-(pyridine-4-carbonyl)-piperidin-3-yl]-1H-indol-6-yl}-methanone,
{3-[1-(3,4-dimethoxy-benzoyl)-piperidin-3-yl]-1H-indol-6-yl}-(4-isopropyl-piperazin-1-yl)-methanone,
(4-isopropyl-piperazin-1-yl)-{3-[1-(pyridine-3-carbonyl)-piperidin-3-yl]-1H-indol-6-yl}-methanone,
(4-isopropyl-piperazin-1-yl)-{3-[1-(4-trifluoromethoxy-benzoyl)-piperidin-3-yl]-1H-indol-6-yl}-methanone,
3-{3-[6-(4-isopropyl-piperazine-1-carbonyl)-1H-indol-3-yl]-piperidin-1-yl}-benzonitrile,
(4-isopropyl-piperazin-1-yl)-{3-[1-(3-methoxy-phenyl)-piperidin-3-yl]-1H-indol-6-yl}-methanone,
[3-(4-isobutyl-morpholin-2-yl)-1H-indol-6-yl]-(4-isopropyl-piperazin-1-yl)-methanone,
[3-(4-isopropyl-morpholin-2-yl)-1H-indol-6-yl]-(4-isopropyl-piperazin-1-yl)-methanone,
(4-isopropyl-piperazin-1-yl)-(3-morpholin-4-ylmethyl-1H-indol-6-yl)-methanone, and pharmaceutically acceptable salts thereof.

Especially preferred are the following compounds:
[3-(1-isobutyl-piperidin-4-yl)-1H-indol-6-yl]-(4-isopropyl-piperazin-1-yl)-methanone; hydrochloride,
(4-isopropyl-piperazin-1-yl)-[3-(1-isopropyl-piperidin-4-yl)-1H-indol-6-yl]-methanone; hydrochloride,
(4-cyclopentyl-piperazin-1-yl)-[3-(1-isopropyl-piperidin-4-yl)-1H-indol-6-yl]-methanone,
[3-(1-cyclopentyl-piperidin-4-yl)-1H-indol-6-yl]-(4-isopropyl-piperazin-1-yl)-methanone,
[3-(1-isobutyl-1,2,3,6-tetrahydro-pyridin-4-yl)-1-isopropyl-1H-indol-6-yl]-(4-isopropyl-piperazin-1-yl)-methanone; hydrochloride,
[1-(2,4-difluoro-phenyl)-3-(1-isobutyl-1,2,3,6-tetrahydro-pyridin-4-yl)-1H-indol-6-yl]-(4-isopropyl-piperazin-1-yl)-methanone,
[1-(2,4-difluoro-phenyl)-3-(1-isobutyl-piperidin-4-yl)-1H-indol-6-yl]-(4-isopropyl-piperazin-1-yl)-methanone,

[3-(1-isobutyl-piperidin-4-yl)-1-(3-trifluoromethyl-phenyl)-1H-indol-6-yl]-(4-isopropyl-piperazin-1-yl)-methanone,
3-[3-(1-isobutyl-piperidin-4-yl)-6-(4-isopropyl-piperazine-1-carbonyl)-indol-1-yl]-benzonitrile,
(4-isopropyl-piperazin-1-yl)-(3-piperidin-2-yl-1H-indol-6-yl)-methanone,
(4-isopropyl-piperazin-1-yl)-(3-morpholin-4-ylmethyl-1H-indol-6-yl)-methanone, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined previously, which process comprises treating a compound of formula I-A

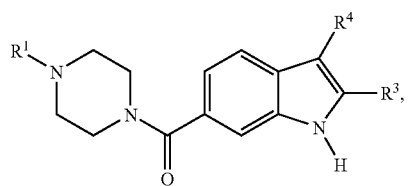

I-A wherein $R^1$, $R^3$ and $R^4$ are as defined herein before, with a suitable base in a suitable solvent under anhydrous conditions and reacting the intermediate anion with a compound of the formula II

$R^2$—X    II, wherein X signifies a leaving group and $R^2$ is selected from the group consisting of (1) lower alkyl, (2) lower halogenalkyl, (3) —SO$_2$—R$^5$, wherein R$^5$ is lower alkyl, phenyl optionally substituted by one or two groups selected from the group consisting of lower alkyl, lower alkoxy, halogen, cyano, lower halogenalkyl and lower halogenalkoxy, (4) —C(O)—(CH$_2$)$_n$-phenyl, wherein the phenyl ring is option- ally substituted by one or two groups selected from the group consisting of lower alkyl, lower alkoxy, halogen, cyano, lower halogenalkyl and lower halogenalkoxy, (5) —(CH$_2$)$_n$-cycloalkyl, (6) pyridyl, and (7) —(CH$_2$)$_n$-phenyl, wherein the phenyl ring is optionally substituted by one, two or three groups independently selected from lower alkyl, lower halogenalkyl, halogen, cyano, lower alkoxy and lower halogenalkoxy; to obtain a compound of formula I-B

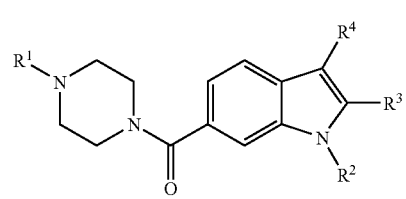

I-B wherein $R^1$, $R^3$ and $R^4$ are as defined herein before and $R^2$ is selected from the group consisting of (1) lower alkyl, (2) lower halogenalkyl, (3) —SO$_2$—R$^5$, wherein R$^5$ is lower alkyl, phenyl optionally substituted by one or two groups selected from the group consisting of lower alkyl, lower alkoxy, halogen, cyano, lower halogenalkyl and lower halogenalkoxy, (4) —C(O)—(CH$_2$)$_n$-phenyl, wherein the phenyl ring is optionally substituted by one or two groups selected from the group consisting of lower alkyl, lower alkoxy, halogen, cyano, lower halogenalkyl and lower halogenalkoxy, (5) —(CH$_2$)$_n$-cycloalkyl, (6) pyridyl, and (7) —(CH$_2$)$_n$-phenyl, wherein the phenyl ring is optionally substituted by one, two or three groups independently selected from lower alkyl, lower halogenalkyl, halogen, cyano, lower alkoxy and lower halogenalkoxy;

and if desired, converting the compound obtained into a pharmaceutically acceptable acid addition salt.

Treating a compound of formula I-A with a suitable base in a suitable solvent under anhydrous conditions means e.g. treating the compound with a base such as sodium hydride, diisopropylethylamine, sodium carbonate or cesium carbonate in a solvent such as N,N-dimethyl acetamide, N,N-dimethylformamide, tetrahydrofuran, diethyl ether, dioxane, acetonitrile or butanone to obtain the intermediate anion which is then reacted with the compound of formula II. The leaving group X can be any halogen group (chlorine, bromine, iodine) or pseudo halogen group (e.g. trifluoromethylmethane-sulfonyl, para-toluenesulfonyl, methanesulfonyl and the like). In case $R^2$ is aryl or heteroaryl (e.g. pyridyl), the presence of a copper catalyst (e.g. copper(II) acetate) may also be needed.

In more detail, the compounds of formula I can be manufactured by the methods given below, by the methods given in the examples or by analogous methods. The preparation of compounds of formula I of the present invention may be carried out in sequential or convergent synthetic routes. The skills required for carrying out the reaction and for purification of the resulting products are known to those skilled in the art. The substituents and indices used in the following description of the processes have the significance given herein before unless indicated to the contrary. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Depending on the respective reactivity of certain intermediates towards certain reaction conditions, the reaction sequences towards more advanced intermediates or final products can be reversed.
Scheme 1
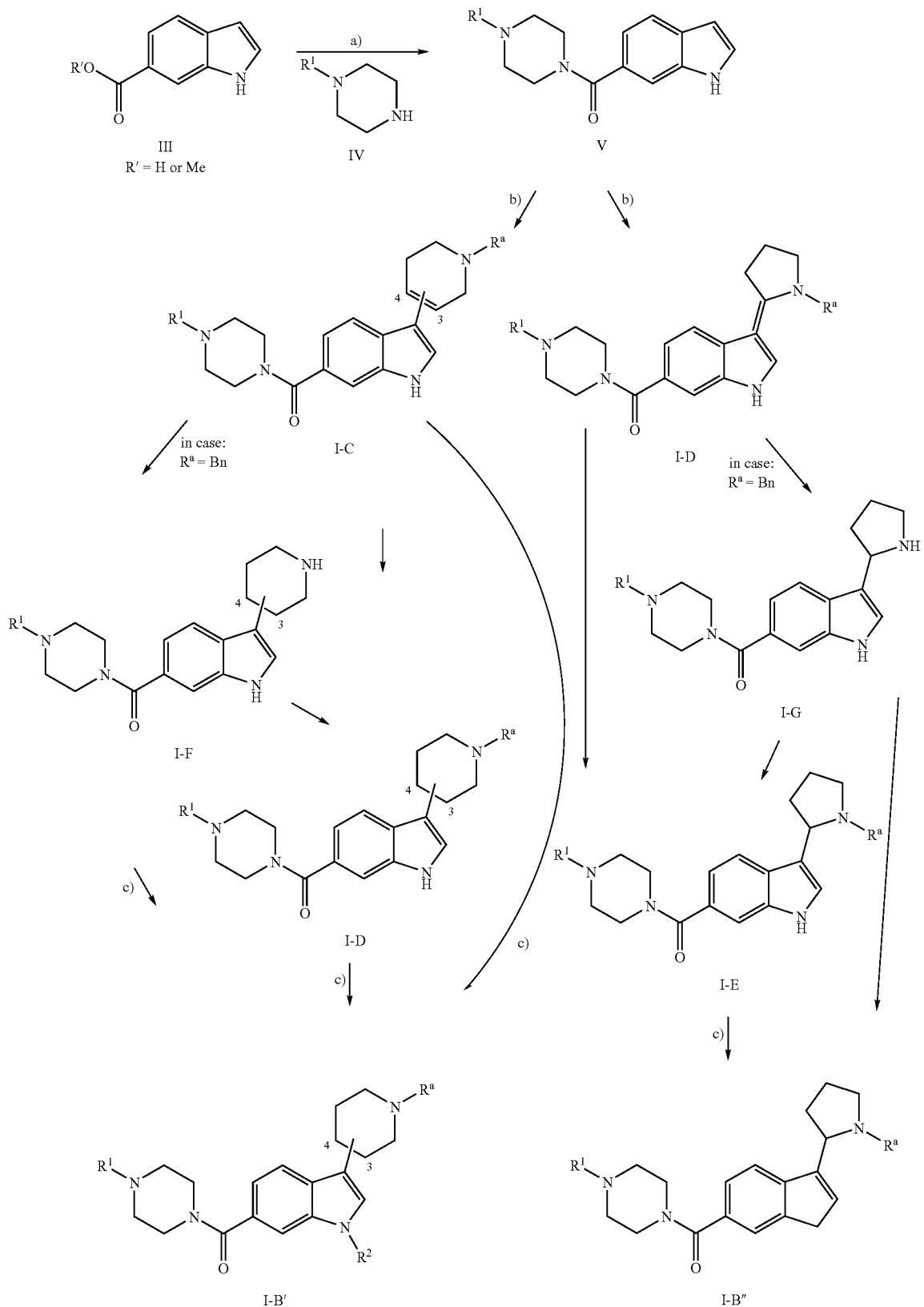

a) Indole-6-carboxylic acid III (R=H) is commercially available and can conveniently be transferred into the respective piperazine amide by amide coupling procedures described in the literature. However, it is convenient to transform the acid functionality through amide coupling with substituted piperazines IV (either commercially available or accessible by methods described in references or by methods known in the art; as appropriate) employing a coupling reagent. The reaction may be carried out in the presence or absence of a solvent and a base. There is no particular restriction on the nature of the solvent to be employed, provided that it has no adverse effect on the reaction or the reagents involved and that it can dissolve the reagents, at least to some extent. Examples for suitable solvents include DMF, THF, dioxane, and the like. Dimethylformamide (DMF) and dioxane are preferred solvents.

There is no particular restriction on the nature of the base used in this stage, and any base commonly used in this type of reaction may equally be employed here. Preferred examples of such bases include triethylamine ($NEt_3$) or diisopropylethylamine (DIPEA). There is no particular restriction on the nature of the coupling reagent used in this stage, and any coupling reagent commonly used in this type of reaction may equally be employed here. Examples of such reducing agents include N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU). Preferably, a coupling reagent selected from the group consisting of 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT) and O-benzotriazol-1-yl-N,N,N',N'-tetramethyluronium tetrafluoroborate (TBTU) is used.

The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the intermediate amides.

b) Functionalisation at the 3 position of the indoles can be achieved under basic conditions with the respective piperidone or also under acidic conditions with the respective pyrrolidone in the presence of an activating agent. Piperidones and pyrrolidones are either commercially available or accessible by methods described in references or by methods known in the art; as appropriate. There is no particular restriction on the nature of the solvent to be employed, provided that it has no adverse effect on the reaction or the reagents involved and that it can dissolve the reagents, at least to some extent. Examples for suitable solvents include methanol, ethanol and the like. In cases where piperidones are employed there is no particular restriction on the nature of the base used in this stage, and any base commonly used in this type of reaction may equally be employed here. Examples of such bases include sodium hydroxide (NaOH), potassium hydroxide (KOH), and the like. In cases where pyrrolidones are employed we find it convenient to utilize an activating agent like phosphoryl chloride ($POCl_3$). Any other activating agent might be equally employed here, provided it has no adverse effect on the reaction. Anyway, the reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield indoles I-C and VI. Indoles I-C are part of the invention and might be the desired end-products. However, further transformation from unsaturated variants, via reduction leads to further saturated indole derivatives I-D and I-E. It is convenient to hydrogenate (varying $H_2$ pressures are applicable) or employ a reducing agent under neutral or acidic conditions in a solvent. Again, there is no particular restriction on the nature of the solvent to be employed, provided that it has no adverse effect on the reaction or the reagents involved and that it can dissolve the reagents, at least to some extent. Examples for suitable solvents include: methanol, ethanol and the like. There is no particular restriction on the nature of the acid used in this stage, and any acid commonly used in this type of reaction may equally be employed here. Examples of such acids include HCl, acetic acid and the like. Typical reducing agents are sodium borohydride, and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield saturated indoles I-D and I-E. In cases were $R^a$ is benzyl, this protecting group might be cleaved off under reductive conditions to yield indole derivatives I-F and I-G that are also part of the invention and the liberated piperidine/pyrrolidine NH might be transformed to indole derivatives in which $R^a$ is not hydrogen. It is convenient either to introduce $R^a$ under reductive conditions with an aldehyde or introduce $R^a$ under basic conditions with an electrophile.

c) The resulting indoles of formula I-C, I-D, I-E, I-F and I-G are part of the invention, however, they might be transferred to indole derivatives I-B' and I-B" in which the indole NH will be substituted. Introduction of a substituent is widely described in literature and methods are known to those in the art. It is convenient to introduce lower alkyl substituents, benzyl substituents, alkyl and arylsulfonyl substituents through a reaction with an alkylating or acylating agent II (either commercially available or accessible by methods described in references or by methods known in the art, as appropriate). Conditions commonly used in such types of transformation are widely described in literature and known to those in the art. The leaving group X can be any halogen group (chlorine, bromine, iodine) or pseudo halogen group (e.g. trifluoromethylmethane-sulfonyl, para-toluenesulfonyl, methanesulfonyl and the like). The reaction might be carried out in the presence or absence of a solvent and preferably in the presence of a base. Solvents like N,N-dimethyl acetamide, N,N-dimethylformamide, tetrahydrofuran, diethyl ether, dioxane, acetonitrile, butanone and the like are conveniently used. There is no particular restriction on the nature of the solvent to be employed, provided that it has no adverse effect on the reaction or the reagents involved and that it can dissolve the reagents, at least to some extent. Usually the reaction is carried out in the presence of a base. Suitable bases include sodium hydride, diisopropylethylamine, sodium carbonate, cesium carbonate and the like. The reaction can take place over a wide range of temperatures and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the desired compounds of formula I-B' or 1-B". It is convenient to introduce aryl substituents under copper catalysis with aryl-iodides or heteroaryl iodides. Alternatively, a compound of formula I-C, I-D, I-E, I-F or I-G can be arylated by a boronic acid or a boronic ester (either commercially available or accessible by methods described in references or by methods known in the art, as appropriate). Conditions commonly used in such types of transformation are described in literature and known to those in the art.

Indole derivatives of formula I-H or I-J wherein $R^2$ comprises a morpholine ring can be prepared according to the sequence displayed in scheme 2.

The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the indole derivatives VII.

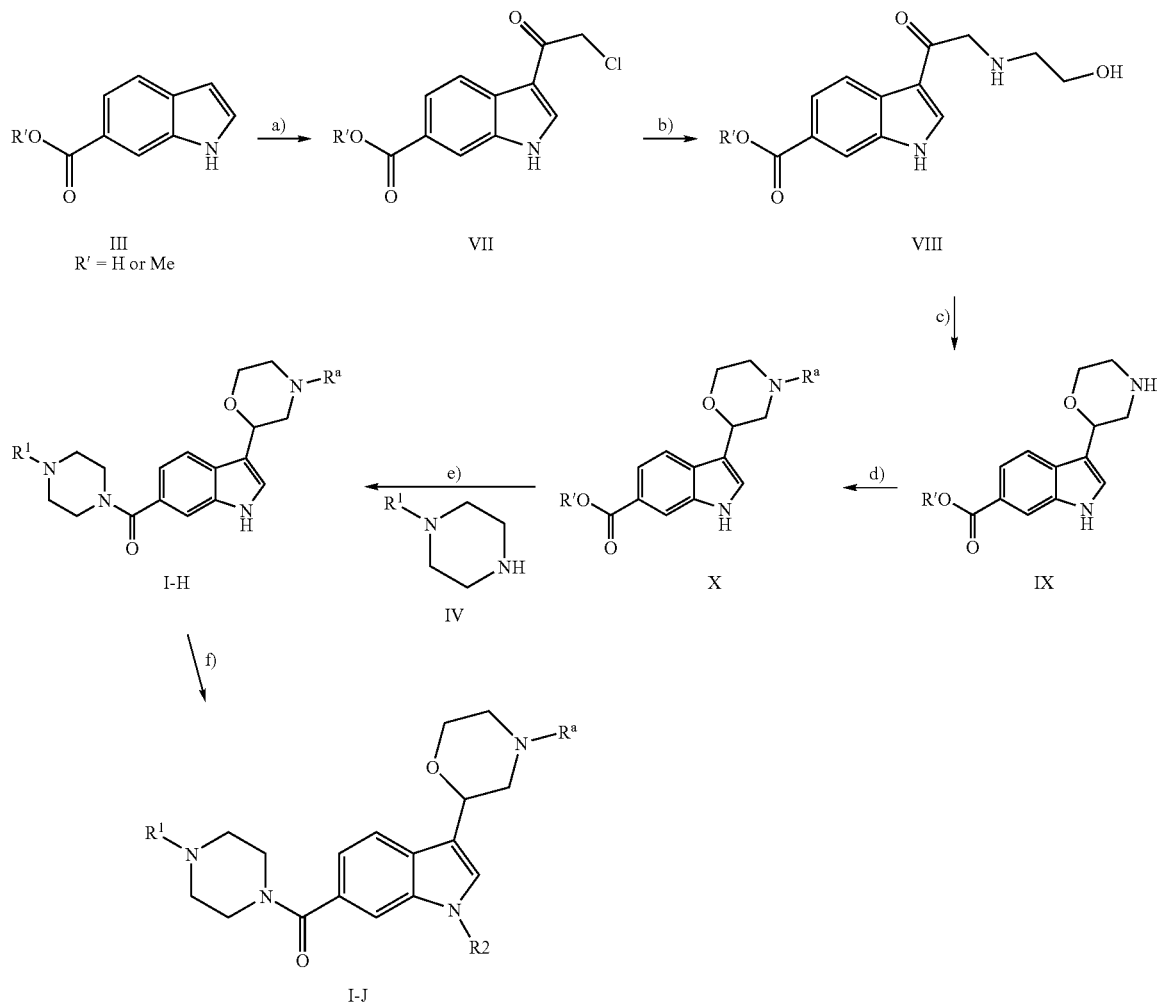

a) Indole-6-carboxylic acid III (R=H) is commercially available and can conveniently be transferred into the respective indole derivative VII by reaction of III with chloro acetyl chloride in the presence or absence of a solvent generally employing a Lewis acid. There is no particular restriction on the nature of the solvent to be employed, provided that it has no adverse effect on the reaction or the reagents involved and that it can dissolve the reagents, at least to some extent. Examples for suitable solvents include DCM, and the like.

There is no particular restriction on the nature of the Lewis acid used in this stage, and any Lewis acid commonly used in this type of reaction may equally be employed here. Preferred examples of such bases include zinc chloride.

b) Subsequent transformation of the α-chloro substituent in indoles VII to the respective indole derivative VIII can be achieved by reaction of VII with ethanolamine in the presence or the absence of a solvent. Preferably no solvent is employed at this stage. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the indole derivatives VIII.

c) Cyclisation of indole derivatives VIII to the respective indole derivatives IX can conveniently be carried out under reductive conditions in the presence of a solvent. Any solvent commonly used for such transformations can be employed. Preferred solvents include methanol and the like. Any commonly used reducing agent can be employed. Preferred reducing agents include sodium borohydride and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the indole derivatives IX.

d) Indole derivatives IX can conveniently be transferred to the respective indole derivatives X by substitution of the free morpholine NH by reductive amination under acidic conditions or by reaction under basic conditions and an electrophile. Any suitable aldehyde or ketone can be reacted under conditions commonly used at such a stage in the presence or the absence of a solvent and acid and in the presence of a reducing agent. Any commonly used solvent might equally be employed at this stage. Preferred solvents include methanol and the like. There is no particular restriction on the nature of the acid used in this stage, and any acid commonly used in this type of reaction may equally be employed here. Examples of such acids include HCl, acetic acid and the like. Typical reducing agents are sodium borohydride, and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield indoles X.

e) Indole derivatives X can conveniently be transferred into the respective piperazine amide I-H by amide coupling procedures described in literature. However, it is convenient to transform the acid functionality (liberated from the respective ester under basic or acidic condition, as described elsewhere) through amide coupling with substituted piperazines IV (either commercially available or accessible by methods described in references or by methods known in the art; as appropriate) employing a coupling reagent. The reaction may be carried out in the presence or absence of a solvent and a base. There is no particular restriction on the nature of the solvent to be employed, provided that it has no adverse effect on the reaction or the reagents involved and that it can dissolve the reagents, at least to some extent. Examples for suitable solvents include DMF, THF, dioxane, and the like. Dimethylformamide (DMF) and dioxane are preferred solvents.

There is no particular restriction on the nature of the base used in this stage, and any base commonly used in this type of reaction may equally be employed here. Preferred examples of such bases include triethylamine (NEt$_3$) or diisopropylethylamine (DIPEA). There is no particular restriction on the nature of the coupling reagent used in this stage, and any coupling reagent commonly used in this type of reaction may equally be employed here. Examples of such reducing agents include N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU). Preferably, a coupling reagent selected from the group consisting of 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT) and O-benzotriazol-1-yl-N,N,N',N'-tetramethyluronium tetrafluoroborate (TBTU) is used.

The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the intermediate amides Neu8.

f) The resulting indoles of formula I-H are part of the invention, however, they might be transferred to indole derivatives I-J in which the indole NH will be substituted. Introduction of a substituent is widely described in literature and methods are known to those in the art. It is convenient to introduce lower alkyl substituents, benzyl substituents, alkyl and arylsulfonyl substituents through a reaction with an alkylating or acylating agent II (either commercially available or accessible by methods described in references or by methods known in the art, as appropriate). Conditions commonly used in such types of transformation are widely described in literature and known to those in the art. The leaving group X can be any halogen group (chlorine, bromine, iodine) or pseudo halogen group (e.g. trifluoromethylmethane-sulfonyl, paratoluenesulfonyl, methanesulfonyl and the like). The reaction might be carried out in the presence or absence of a solvent and preferably in the presence of a base. Solvents like N,N-dimethyl acetamide, N,N-dimethylformamide, tetrahydrofuran, diethyl ether, dioxane, acetonitrile, butanone and the like are conveniently used. There is no particular restriction on the nature of the solvent to be employed, provided that it has no adverse effect on the reaction or the reagents involved and that it can dissolve the reagents, at least to some extent. Usually the reaction is carried out in the presence of a base. Suitable bases include sodium hydride, diisopropylethylamine, sodium carbonate, cesium carbonate and the like. The reaction can take place over a wide range of temperatures and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the desired compounds of formula I-J. It is convenient to introduce aryl substituents under copper catalysis with aryl-iodides or heteroaryl iodides. Alternatively, a compound of formula I-H can be arylated by a boronic acid or a boronic ester (either commercially available or accessible by methods described in references or by methods known in the art, as appropriate). Conditions commonly used in such types of transformation are described in literature and known to those in the art.

Any of the previously mentioned reaction steps might be used in a different order depending on the reactivity of the respective indole derivatives.

The compounds of formula I can contain several asymmetric centres and can be present in the form of optically pure enantiomers, mixtures of enantiomers such as, e.g. racemates, optically pure diastereomers, mixtures of diastereomers, diastereomeric racemates or mixtures of diastereomeric racemates. The optically active forms can be obtained for example by resolution of the racemates, by asymmetric synthesis or asymmetric chromatography (chromatography with a chiral adsorbent or eluant).

As described previously, the compounds of formula I of the present invention can be used as medicaments for the treatment and/or prevention of diseases which are associated with the modulation of H3 receptors.

In this context, the expression diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In a preferable aspect, the expression diseases associated with modulation of H3 receptors' relates to obesity, metabolic syndrome (syndrome X), and other eating disorders, with obesity being especially preferred.

The invention therefore also relates to pharmaceutical compositions comprising a compound as defined previously and a pharmaceutically acceptable carrier and/or adjuvant.

Further, the invention relates to compounds as defined previously for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined previously for the treatment and/or prevention of diseases which are associated with the modulation of H3 receptors.

In addition, the invention relates to the use of compounds of formula I as defined previously for the preparation of medicaments for the treatment and/or prevention of diseases which are associated with the modulation of H3 receptors. The use of compounds of formula I as defined previously for the preparation of medicaments for the treatment and/or prevention of obesity is preferred.

Furthermore, the present invention relates to the use of a compound of formula I for the manufacture of a medicament for the treatment and prevention of obesity in a patient who is also receiving treatment with a lipase inhibitor and particularly, wherein the lipase inhibitor is orlistat.

It is a further preferred object of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the previously agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, a minorex, amphechloral, amphetamine, axokine, benzphetamine, bupropion, chlorphentermine, clobenzolex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a medicament for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an object of the present invention.

The use of a compound of formula I in the manufacture of a medicament for the treatment and prevention of obesity in a patient who is also receiving treatment with a lipase inhibitor, preferably with tetrahydrolipstatin, is also an object of the present invention.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an object of the invention is the method as described previously for the simultaneous, separate or sequential administration of a compound according to formula I and a lipase inhibitor, particularly tetrahydrolipstatin.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglimide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; 8) α-Glucosidase inhibitors such as acarbose (precose) or miglitol (glyset), and the like.

Also an object of the invention is the method as described previously for the simultaneous, separate or sequential administration of a compound according to formula I and a therapeutically effective amount of an anti-diabetic agent.

The use of a compound of formula I in the manufacture of a medicament for the treatment and prevention of Type II diabetes in a patient who is also receiving treatment with an anti-diabetic agent is also an object of the present invention.

It is a further preferred object to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6) lipoprotein synthesis inhibitors such as niacin, and the like; and 7) niacin receptor agonists such as nicotinic acid, and the like.

Also an object of the invention is the method as described previously for the simultaneous, separate or sequential administration of a compound according to formula I and a therapeutically effective amount of a lipid lowering agent.

The use of a compound of formula I in the manufacture of a medicament for the treatment and prevention of dyslipidemias in a patient who is also receiving treatment with a lipid lowering agent, is also an object of the present invention.

It is a further preferred object to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin II Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyldopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetamide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (symcor) and the like; 7) Tyrosine Hydroxylase Inhibitors, including metyrosine (demser), and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan, A308165, and the like.

Also an object of the invention is the method as described previously for the simultaneous, separate or sequential administration of a compound according to formula I and a therapeutically effective amount of a anti-hypertensive agent.

The use of a compound of formula I in the manufacture of a medicament for the treatment and prevention of hypertension in a patient who is also receiving treatment with an anti-hypertensive agent, is also an object of the present invention.

As described previously, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula (I).

Binding assay with $^3$H-(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 μg protein/well) was incubated with increasing concentrations of $^3$H(R) α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 μl. The incubation was followed by rapid filtration on GF/B filters (pre-soaked with 100 μl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard top-counter after shaking the plates for two hours at 200 rpm at room temperature.

Binding Buffer: 50 mM Tris-HCl pH 7.4 and 5 mM $MgCl_2 \times 6H_2O$ pH 7.4.

Washing Buffer: 50 mM Tris-HCl pH 7.4 and 5 mM $MgCl_2 \times 6H_2O$ and 0.5 M NaCl pH 7.4.

Indirect measurement of affinity of H3R inverse agonists: twelve increasing concentrations (ranging from 10 μM to 0.3 nM) of the selected compounds were always tested in competition binding experiments using membrane of the human HR3-CHO cell line. An appropriate amount of protein, e.g. approximately 500 cpm binding of RAMH at Kd, were incubated for 1 hour at room temperature in 250 μl final volume in 96-well plates in presence of $^3$H(R)α-Methylhistamine (1 nM final concentration=Kd). Non-specific binding was determined using a 200 fold excess of cold (R)α-Methylhistamine dihydrobromide.

All compounds were tested at a single concentration in duplicate. Compounds that showed an inhibition of [$^3$H]-RAMH by more than 50% were tested again to determine $IC_{50}$ in a serial dilution experiment, meaning concentrations were spanning 10 points starting from $4.6 \times 10^{-6}$ M to $1.0 \times 10^{-9}$ M. The dilution factor was 1/2.15 for the whole series. The concentration at which 50% inhibition of the radioligand $^3$H(R)α-methylhistamine is obtained (the $IC_{50}$) is determined from the linear regression of a plot of the logarithm of the concentration versus percent inhibition measured for the different concentrations. Ki's were calculated from $IC_{50}$ based on Cheng-Prusoff equation (Cheng, Y, Prusoff, W H (1973) Biochem Pharmacol 22, 3099-3108): Ki=IC50/[1+D/Kd] wherein D is the concentration of the radioligand and Kd is the binding constant for the radioligand binding to the receptor under the conditions used in the competition experiment.

The compounds of the present invention exhibit $K_i$ values within the range of about 1 nM to about 1000 nM, preferably of about 1 nM to about 100 nM, and more preferably of about 1 nM to about 30 nM, most preferably of about 1 nM to about 20 nM. The following table shows measured values for some selected compounds of the present invention.

|  | $K_i$ (nM) |
| --- | --- |
| Example 2 | 24.3 |
| Example 35 | 33.1 |
| Example 54 | 17.6 |

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoA1 mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoA1 mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

The following are a list of abbreviations and/or acronyms with their corresponding definitions used in the following examples: TBTU=O-benzotriazol-1-yl-N,N,N',N'-tetramethyluronium tetrafluoroborate; DIPEA=diisopropylethylamine; THF=tetrahydrofuran; DCM=dichloromethane; MeOH=methanol; MS=mass spectrometry; and (MH$^+$)=the molecular weight of the compound plus a proton.

Example 1

[3-(1-Isobutyl-1,2,3,6-tetrahydro-pyridin-4-yl)-1H-indol-6-yl]-(4-isopropyl-piperazin-1-yl)-methanone; hydrochloride a) Step 1: (1H-Indol-6-yl)-(4-isopropyl-piperazin-1-yl)-methanone A mixture of 1 g (6 mmol) indole-6-carboxylic acid (commercially available), 0.96 g (0.7 mmol) 1-(2-propyl)-piperazine (commercially available), 2.39 g (7 mmol) TBTU and 4 g (31 mmol) DIPEA in 30 ml THF was stirred for 1 h at room temperature. After evaporation of all volatiles Na$_2$CO$_3$ (10% aq.) and ethyl acetate was added. The mixture was extracted with ethyl acetate and the combined organic fractions were washed with NaCl (sat. aq.), dried with Na$_2$SO$_4$ and evaporated to dryness. The residue was purified by flash column chromatography on silica eluting with a mixture formed from DCM, MeOH and NH$_3$ aq. to yield after evaporation of the combined product fractions 1.64 g (97%) of the title compound as light yellow solid. MS (m/e): 272.5 (MH$^+$).

b) Step 2: [3-(1-Isobutyl-1,2,3,6-tetrahydro-pyridin-4-yl)-1H-indol-6-yl]-(4-isopropyl-piperazin-1-yl)-methanone; hydrochloride A mixture of 0.2 g (0.8 mmol) (1H-indol-6-yl)-(4-isopropyl-piperazin-1-yl)-methanone and 0.23 g (1.48 mmol) 1-(2-methylpropyl)-4-piperidone (commercially available) in 1.6 mL 1.42 N KOH/methanol solution was stirred at 50° C. for 17 h. Water and ethyl acetate were added and the mixture was extracted with ethyl acetate and the combined organic fractions were washed with NaCl (sat. aq.), dried with Na$_2$SO$_4$ and evaporated to dryness. The residue was purified by column chromatography on isolute eluting with a mixture formed from DCM, MeOH and NH$_3$ aq. to yield after transforming into the respective HCL salt by addition of HCl in MeOH and precipitation from i-propanol and diethyl ether 0.19 g (58%) of the title compound as light yellow solid. MS (m/e): 409.3 (MH$^+$).

Example 2

[3-(1-Isobutyl-piperidin-4-yl)-1H-indol-6-yl]-(4-isopropyl-piperazin-1-yl)-methanone; hydrochloride 0.18 g (0.4 mmol) [3-(1-isobutyl-1,2,3,6-tetrahydro-pyridin-4-yl)-1H-indol-6-yl]-(4-isopropyl-piperazin-1-yl)-methanone; hydrochloride was hydrogenated with H$_2$ over Pd/C (10%) in 50 mL methanol for 18 h at room temperature. After filtration and washing of the catalyst with methanol the solution was evaporated to dryness. The title compound was crystallized from i-propanol and diethyl ether and dried. 0.17 g (92%) was yielded as light yellow solid. MS (m/e): 411.3 (MH$^+$).

Example 3

(4-Isopropyl-piperazin-1-yl)-[3-(1-isopropyl-piperidin-4-yl)-1H-indol-6-yl]-methanone; hydrochloride a) Step 1: (4-Isopropyl-piperazin-1-yl)-[3-(1-isopropyl-1,2,3,6-tetrahydro-pyridin-4-yl)-1H-indol-6-yl]-methanone; hydrochloride According to the procedure described for the synthesis of [3-(1-isobutyl-1,2,3,6-tetrahydro-pyridin-4-yl)-1H-indol-6-yl]-(4-isopropyl-piperazin-1-yl)-methanone; hydrochloride (Example 1; step 2) the title compound was prepared from (1H-indol-6-yl)-(4-isopropyl-piperazin-1-yl)-methanone and 1-(2-propyl)-4-piperidone (commercially available). MS (m/e): 395.3 (MH$^+$).

b) Step 2: (4-Isopropyl-piperazin-1-yl)-[3-(1-isopropyl-piperidin-4-yl)-1H-indol-6-yl]-methanone; hydrochloride According to the procedure described for the synthesis of [3-(1-isobutyl-piperidin-4-yl)-1H-indol-6-yl]-(4-isopropyl-piperazin-1-yl)-methanone; hydrochloride (Example 2) the title compound was prepared from (4-Isopropyl-piperazin-1-yl)-[3-(1-isopropyl-1,2,3,6-tetrahydro-pyridin-4-yl)-1H-indol-6-yl]-methanone; hydrochloride through hydrogenation. MS (m/e): 397.4 (MH$^+$).

Example 4

[3-(1-Benzyl-1,2,3,6-tetrahydro-pyridin-4-yl)-1H-indol-6-yl]-(4-isopropyl-piperazin-1-yl)-methanone a) Step 1: 3-(1-Benzyl-1,2,3,6-tetrahydro-pyridin-4-yl)-1H-indole-6-carboxylic acid According to the procedure described for the synthesis of [3-(1-isobutyl-1,2,3,6-tetrahydro-pyridin-4-yl)-1H-indol-6-yl]-(4-isopropyl-piperazin-1-yl)-methanone; hydrochloride (Example 1; step 2) the title compound was prepared from indole-6-carboxylic acid (commercially available) and 1-benzyl-4-piperidone (commercially available). MS (m/e): 333.2 (MH$^+$).

b) Step 2: [3-(1-Benzyl-1,2,3,6-tetrahydro-pyridin-4-yl)-1H-indol-6-yl]-(4-isopropyl-piperazin-1-yl)-methanone According to the procedure described for the synthesis of (1H-indol-6-yl)-(4-isopropyl-piperazin-1-yl)-methanone (example 1, step 1) the title compound was prepared from 3-(1-enzyl-1,2,3,6-tetrahydro-pyridin-4-yl)-1H-indole-6-carboxylic acid and 1-(2-propyl)-piperazine (commercially available). MS (m/e): 443.4 (MH⁺).

Example 5

[3-(1-Benzyl-1,2,3,6-tetrahydro-pyridin-4-yl)-1H-indol-6-yl]-(4-cyclopentyl-piperazin-1-yl)-methanone According to the procedure described for the synthesis of [3-(1-benzyl-1,2,3,6-tetrahydro-pyridin-4-yl)-1H-indol-6-yl]-(4-isopropyl-piperazin-1-yl)-methanone (example 4, step 2) the title compound was prepared from 3-(1-benzyl-1,2,3,6-tetrahydro-pyridin-4-yl)-1H-indole-6-carboxylic acid and 1-cyclopentyl-piperazine (commercially available). MS (m/e): 469.3 (MH⁺).

Example 6

(4-Isopropyl-piperazin-1-yl)-[3-(1-methyl-piperidin-4-yl)-1H-indol-6-yl]-methanone And Example 7

(4-Isopropyl-piperazin-1-yl)-(3-piperidin-4-yl-1H-indol-6-yl)-methanone; hydrochloride A mixture of 0.2 g (0.45 mmol) [3-(1-benzyl-1,2,3,6-tetrahydro-pyridin-4-yl)-1H-indol-6-yl]-(4-isopropyl-piperazin-1-yl)-methanone, 0.1 mg Pd/C (10%) and 0.42 g formic acid in 25 ml methanol was hydrogenated with H₂ (1 bar) for 45 h at room temperature. After filtration of the catalyst the mixture was evaporated to dryness, treated with methanol and aqueous ammonia and again evaporated to dryness. The residue was purified by flash column chromatography on silica eluting with a mixture formed from dichlormethane (DCM), methanol (MeOH) and NH₃ aq. to yield after evaporation of the respectively combined product fractions 48 mg (29%) of (4-isopropyl-piperazin-1-yl)-[3-(1-methyl-piperidin-4-yl)-1H-indol-6-yl]-methanone (example 6), MS (m/e): 369.2 (MH⁺), and 127 mg (72%) (4-isopropyl-piperazin-1-yl)-(3-piperidin-4-yl-1H-indol-6-yl)-methanone, hydrochloride (example 7), MS (m/e): 355.2 (MH⁺) (converted from the free base to the respective mono hydrochloride by addition of methanol and HCl and subsequent evaporation).

Example 8

(4-Cyclopentyl-piperazin-1-yl)-(3-piperidin-4-yl-1H-indol-6-yl)-methanone

A mixture of 0.3 g (0.64 mmol) [3-(1-benzyl-1,2,3,6-tetrahydro-pyridin-4-yl)-1H-indol-6-yl]-(4-cyclopentyl-piperazin-1-yl)-methanone and 70 mg Pd/C (10%) in 25 mL acetic acid was hydrogenated with H₂ (1 bar) for 16 h at 60° C. After filtration of the catalyst the mixture was evaporated to dryness. The residue was treated with methanol and aqueous ammonia and evaporated again and subsequently purified by flash column chromatography eluting with a mixture formed from DCM, MeOH and NH₃ aq. to yield after evaporation of the combined product fractions 0.195 g (80%) of the title compound as white foam. MS (m/e): 381.3 (MH⁺).

Example 9

(4-Isopropyl-piperazin-1-yl)-(3-piperidin-3-yl-1H-indol-6-yl)-methanone

A mixture of 1 g (6 mmol) indole-6-carboxylic acid, 2.3 g (37 mmol) KOH pellets and 4.5 g (19 mmol) 1-benzyl-3-piperidone in 25 mL methanol was heated to reflux for 65 h. After evaporation of the volatiles water was added and the pH was adjusted to pH=6. The precipitate was filtered of and triturated with ethyl acetate and THF. The combined organic layers were washed with NaCl (sat. aq.), dried with Na₂SO₄ and evaporated to dryness. 2.4 g (7 mmol) O-benzotriazol-1-yl-N,N,N',N'-tetramethyluronium tetrafluoroborate (TBTU), 0.96 g (7 mmol) 1-(2-propyl)-piperazine, 6.5 ml (38 mmol) diisopropylethylamine (DIPEA) and 100 mL THF was added and the mixture was stirred for 16 h at room temperature. Na₂CO₃ aq. was added and the mixture was extracted with ethyl actetate. The combined organic layers were washed with NACl (sat. aq.), dried with Na₂SO₄ and evaporated to dryness. The intermediate was concentrated through column chromatography on silica eluting with a mixture formed from DCM, MeOH and NH₃ aq. and used in the subsequent hydrogenation step. 100 mL acetic acid and 50 mg Pd/C (10%) was added and the mixture was hydrogenated with H₂ (1 bar) for 16 h at 60° C. After filtration of the catalyst the mixture was evaporated to dryness. The residue was treated with water, Na₂CO₃ (10% aq.) and extracted with DCM. The combined organic layers were dried with Na₂SO₄, evaporated to dryness and subsequently purified by flash column chromatography eluting with a mixture formed from DCM, MeOH and NH₃ aq. to yield after evaporation of the combined product fractions 0.78 g (35%) of the title compound as light brown foam. MS (m/e): 355.2 (MH⁺).

Example 10

(4-Isopropyl-piperazin-1-yl)-[3-(1-isopropyl-piperidin-3-yl)-1H-indol-6-yl]-methanone A mixture of 50 mg (0.14 mmol) (4-isopropyl-piperazin-1-yl)-(3-piperidin-3-yl-1H-indol-6-yl)-methanone, 23 mg (0.16 mmol) K₂CO₃ and 97 mg (0.57 mmol) 2-iodo-propane in 2 mL THF was stirred for 17 h at 60° C. Isolute sorbent was added and the mixture evaporated. The residue was purified by flash column chromatography on silica eluting with a mixture formed from dichlormethane (DCM), MeOH and NH₃ aq. to yield after evaporation of the combined product fractions 36 mg (64%) of the title compound as off-white foam. MS (m/e): 397.3 (MH⁺).

Example 11

[3-(1-Cyclopentyl-piperidin-3-yl)-1H-indol-6-yl]-(4-isopropyl-piperazin-1-yl)-methanone A mixture of 50 mg (0.14 mmol) (4-isopropyl-piperazin-1-yl)-(3-piperidin-3-yl-1H-indol-6-yl)-methanone, 14 mg (0.16 mmol) cyclopentanone, 45 mg (0.2 mmol) sodium triacteoxyborohydride and 13 mg (0.2 mmol) acetic acid in 3 mL THF was stirred for 16 h at room temperature. Water and Na₂CO₃ aq. was added and the mixture was extracted with ethyl acetate. The organic layers were dried with Na₂SO₄ and evaporated to dryness. The residue was purified by flash column chromatography eluting with a mixture formed from DCM, MeOH and NH₃ aq. to yield after evaporation of the combined product fractions 41 mg (69%) of the title compound as light yellow foam. MS (m/e): 423.3 (MH⁺).

Example 12

(4-Cyclopentyl-piperazin-1-yl)-[3-(1-isopropyl-piperidin-4-yl)-1H-indol-6-yl]-methanone According to the procedure described for the synthesis of (4-isopropyl-piperazin-1-yl)-[3-(1-isopropyl-piperidin-3-yl)-1H-indol-6-yl]-methanone (Example 10) the title compound was prepared from (4-cyclopentyl-piperazin-1-yl)-(3-piperidin-4-yl-1H-indol-6-yl)-methanone (example 8) and 2-iodopropane. MS (m/e): 423.2 (MH⁺).

Example 13

[3-(1-Cyclopentyl-piperidin-4-yl)-1H-indol-6-yl]-(4-isopropyl-piperazin-1-yl)-methanone According to the procedure described for the synthesis of [3-(1-cyclopentyl-piperidin-3-yl)-1H-indol-6-yl]-(4-isopropyl-piperazin-1-yl)-methanone (example 11) the title compound was prepared from (4-isopropyl-piperazin-1-yl)-(3-piperidin-4-yl-1H-indol-6-yl)-methanone; hydrochloride (example 6) and cyclopentanone (commercially available). MS (m/e): 423.2 (MH⁺).

Example 14

(4-Cyclopentyl-piperazin-1-yl)-[3-(1-cyclopentyl-piperidin-4-yl)-1H-indol-6-yl]-methanone According to the procedure described for the synthesis of [3-(1-cyclopentyl-piperidin-3-yl)-1H-indol-6-yl]-(4-isopropyl-piperazin-1-yl)-methanone (example 11) the title compound was prepared from (4-cyclopentyl-piperazin-1-yl)-(3-piperidin-4-yl-1H-indol-6-yl)-methanone (example 8) and cyclopentanone (commercially available). MS (m/e): 449.3 (MH⁺).

Example 15

[3-(1-Cyclobutyl-piperidin-4-yl)-1H-indol-6-yl]-(4-isopropyl-piperazin-1-yl)-methanone According to the procedure described for the synthesis of [3-(1-cyclopentyl-piperidin-3-yl)-1H-indol-6-yl]-(4-isopropyl-piperazin-1-yl)-methanone (example 11) the title compound was prepared from (4-isopropyl-piperazin-1-yl)-(3-piperidin-4-yl-1H-indol-6-yl)-methanone; hydrochloride (example 6) and cyclobutanone (commercially available). MS (m/e): 409.3 (MH⁺).

Example 16

[3-(1-Cyclobutyl-piperidin-4-yl)-1H-indol-6-yl]-(4-cyclopentyl-piperazin-1-yl)-methanone According to the procedure described for the synthesis of [3-(1-cyclopentyl-piperidin-3-yl)-1H-indol-6-yl]-(4-isopropyl-piperazin-1-yl)-methanone (example 11) the title compound was prepared from (4-cyclopentyl-piperazin-1-yl)-(3-piperidin-4-yl-1H-indol-6-yl)-methanone (example 8) and cyclobutanone (commercially available). MS (m/e): 435.3 (MH⁺).

Example 17

[3-(1-Cyclobutyl-piperidin-3-yl)-1H-indol-6-yl]-(4-isopropyl-piperazin-1-yl)-methanone According to the procedure described for the synthesis of [3-(1-cyclopentyl-piperidin-3-yl)-1H-indol-6-yl]-(4-isopropyl-piperazin-1-yl)-methanone (example 11) the title compound was prepared from (4-isopropyl-piperazin-1-yl)-(3-piperidin-3-yl-1H-indol-6-yl)-methanone (example 9) and cyclobutanone (commercially available). MS (m/e): 409.3 (MH⁺).

Example 18

[3-(1-Ethyl-piperidin-4-yl)-1H-indol-6-yl]-(4-isopropyl-piperazin-1-yl)-methanone According to the procedure described for the synthesis of (4-isopropyl-piperazin-1-yl)-[3-(1-isopropyl-piperidin-3-yl)-1H-indol-6-yl]-methanone (Example 10) the title compound was prepared from (4-isopropyl-piperazin-1-yl)-(3-piperidin-4-yl-1H-indol-6-yl)-methanone; hydrochloride (example 7) and iodoethane (commercially available). MS (m/e): 383.3 (MH⁺).

Example 19

(4-Isopropyl-piperazin-1-yl)-[3-(1-propyl-piperidin-4-yl)-1H-indol-6-yl]-methanone According to the procedure described for the synthesis of (4-isopropyl-piperazin-1-yl)-[3-(1-isopropyl-piperidin-3-yl)-1H-indol-6-yl]-methanone (Example 10) the title compound was prepared from (4-isopropyl-piperazin-1-yl)-(3-piperidin-4-yl-1H-indol-6-yl)-methanone; hydrochloride (example 7) and iodopropane (commercially available). MS (m/e): 397.4 (MH⁺).

Example 20

{4-[6-(4-isopropyl-piperazine-1-carbonyl)-1H-indol-3-yl]-piperidin-1-yl}-acetonitrile According to the procedure described for the synthesis of (4-isopropyl-piperazin-1-yl)-[3-(1-isopropyl-piperidin-3-yl)-1H-indol-6-yl]-methanone (Example 10) the title compound was prepared from (4-isopropyl-piperazin-1-yl)-(3-piperidin-4-yl-1H-indol-6-yl)-methanone; hydrochloride (example 7) and bromoacetonitrile (commercially available). MS (m/e): 394.2 (MH⁺).

Example 21

{3-[1-(2,2-Difluoro-ethyl)-piperidin-4-yl]-1H-indol-6-yl}-(4-isopropyl-piperazin-1-yl)-methanone According to the procedure described for the synthesis of (4-isopropyl-piperazin-1-yl)-[3-(1-isopropyl-piperidin-3-yl)-1H-indol-6-yl]-methanone (Example 10) the title compound was prepared from (4-isopropyl-piperazin-1-yl)-(3-piperidin-4-yl-1H-indol-6-yl)-methanone; hydrochloride (example 7) and 2-bromo-1,1-difluoroethane (commercially available). MS (m/e): 419.3 (MH⁺).

Example 22

(4-Isopropyl-piperazin-1-yl)-{3-[1-(2-methoxy-ethyl)-piperidin-4-yl]-1H-indol-6-yl=-methanone According to the procedure described for the synthesis of (4-isopropyl-piperazin-1-yl)-[3-(1-isopropyl-piperidin-3-yl)-1H-indol-6-yl]-methanone (Example 10) the title compound was prepared from (4-isopropyl-piperazin-1-yl)-(3-piperidin-4-yl-1H-indol-6-yl)-methanone; hydrochloride (example 7) and 2-bromoethylmethyl ether (commercially available). MS (m/e): 413.4 (MH⁺).

Example 23

(4-Cyclopentyl-piperazin-1-yl)-[3-(1-propyl-piperidin-4-yl)-1H-indol-6-yl]-methanone According to the procedure described for the synthesis of (4-isopropyl-piperazin-1-yl)-[3-(1-isopropyl-piperidin-3-yl)-1H-indol-6-yl]-methanone (Example 10) the title compound was prepared from [3-(1-cyclopentyl-piperidin-3-yl)-1H-indol-6-yl]-(4-isopropyl-piperazin-1-yl)-methanone (example 11) and iodopropane (commercially available). MS (m/e): 423.4 (MH⁺).

Example 24

(4-Cyclopentyl-piperazin-1-yl)-[3-(1-isobutyl-piperidin-4-yl)-1H-indol-6-yl]-methanone According to the procedure described for the synthesis of (4-isopropyl-piperazin-1-yl)-[3-(1-isopropyl-piperidin-3-yl)-1H-indol-6-yl]-methanone (Example 10) the title compound was prepared from [3-(1-cyclopentyl-piperidin-3-yl)-1H-indol-6-yl]-(4-isopropyl-piperazin-1-yl)-methanone (example 11) and 1-iodo-2-methylpropane (commercially available). MS (m/e): 437.4 (MH⁺).

Example 25

(4-Cyclopentyl-piperazin-1-yl)-{3-[1-(2,2-difluoro-ethyl)-piperidin-4-yl]-1H-indol-6-yl}-methanone According to the procedure described for the synthesis of (4-isopropyl-piperazin-1-yl)-[3-(1-isopropyl-piperidin-3-yl)-1H-indol-6-yl]-methanone (Example 10) the title compound was prepared from [3-(1-cyclopentyl-piperidin-3-yl)-1H-indol-6-yl]-(4-isopropyl-piperazin-1-yl)-methanone (example 11) and 2-bromo-1,1-difluoroethane (commercially available). MS (m/e): 445.3 (MH⁺).

Example 26

(4-Cyclopentyl-piperazin-1-yl)-{3-[1-(2-methoxy-ethyl)-piperidin-4-yl]-1H-indol-6-yl}-methanone According to the procedure described for the synthesis of (4-isopropyl-piperazin-1-yl)-[3-(1-isopropyl-piperidin-3-yl)-1H-indol-6-yl]-methanone (Example 10) the title compound was prepared from [3-(1-cyclopentyl-piperidin-3-yl)-1H-indol-6-yl]-(4-isopropyl-piperazin-1-yl)-methanone (example 11) and 2-bromoethylmethyl ether (commercially available). MS (m/e): 439.4 (MH⁺).

Example 27

(4-Isopropyl-piperazin-1-yl)-[3-(1-propyl-piperidin-3-yl)-1H-indol-6-yl]-methanone According to the procedure described for the synthesis of (4-isopropyl-piperazin-1-yl)-[3-(1-isopropyl-piperidin-3-yl)-1H-indol-6-yl]-methanone (Example 10) the title compound was prepared from (4-isopropyl-piperazin-1-yl)-(3-piperidin-3-yl-1H-indol-6-yl)-methanone (example 9) and iodopropane (commercially available). MS (m/e): 397.4 (MH⁺).

Example 28

[3-(1-Isobutyl-piperidin-3-yl)-1H-indol-6-yl]-(4-isopropyl-piperazin-1-yl)-methanone According to the procedure described for the synthesis of (4-isopropyl-piperazin-1-yl)-[3-(1-isopropyl-piperidin-3-yl)-1H-indol-6-yl]-methanone (Example 10) the title compound was prepared from (4-isopropyl-piperazin-1-yl)-(3-piperidin-3-yl-1H-indol-6-yl)-methanone (example 9) and 1-iodo-2-methylpropane (commercially available). MS (m/e): 411.4 (MH⁺).

Example 29

(4-Isopropyl-piperazin-1-yl)-[3-[1-(2-methoxy-ethyl)-piperidin-3-yl]-1H-indol-6-yl]-methanone According to the procedure described for the synthesis of (4-isopropyl-piperazin-1-yl)-[3-(1-isopropyl-piperidin-3-yl)-1H-indol-6-yl]-methanone (Example 10) the title compound was prepared from (4-isopropyl-piperazin-1-yl)-(3-piperidin-3-yl-1H-indol-6-yl)-methanone (example 9) and 2-bromoethylmethyl ether (commercially available). MS (m/e): 413.4 (MH⁺).

Example 30

4-[6-(4-Isopropyl-piperazine-1-carbonyl)-1H-indol-3-yl]-piperidine-1-carboxylic acid diethylamide A mixture of 40 mg (0.11 mmol) (4-isopropyl-piperazin-1-yl)-(3-piperidin-4-yl-1H-indol-6-yl)-methanone; hydrochloride (example 7), 17 mg (0.125 mmol) diethylcabamoyl chloride (commercially available) and 14 mg (0.138 mmol) NEt₃ in 3 ml THF was stirred for 2 h at room temperature. Isolute was added and the mixture was evaporated to dryness. The residue was purified by flash column chromatography on silica eluting with a mixture formed from DCM, MeOH and NH₃ aq. to yield after evaporation of the combined product fractions 47 mg (92%) of the title compound as white foam. MS (m/e): 454.2 (MH⁺).

Example 31

[3-(1-Benzyl-piperidin-4-yl)-1H-indol-6-yl]-(4-isopropyl-piperazin-1-yl)-methanone According to the procedure described for the synthesis of [3-(1-cyclopentyl-piperidin-3-yl)-1H-indol-6-yl]-(4-isopropyl-piperazin-1-yl)-methanone (example 11) the title compound was prepared from (4-isopropyl-piperazin-1-yl)-(3-piperidin-4-yl-1H-indol-6-yl)-methanone; hydrochloride (example 7) and benzaldehyde (commercially available). MS (m/e): 445.3 (MH⁺).

Example 32

1-{4-[6-(4-Isopropyl-piperazine-1-carbonyl)-1H-indol-3-yl]-piperidin-1-yl}-ethanone According to the procedure described for the synthesis of 4-[6-(4-isopropyl-piperazine-1-carbonyl)-1H-indol-3-yl]-piperidine-1-carboxylic acid diethylamide (example 30) the title compound was prepared from (4-isopropyl-piperazin-1-yl)-(3-piperidin-4-yl-1H-indol-6-yl)-methanone; hydrochloride (example 7) and acetylchloride (commercially available). MS (m/e): 397.2 (MH$^+$).

Example 33

4-Isopropyl-piperazin-1-yl)-[3-(1-methanesulfonyl-piperidin-4-yl)-1H-indol-6-yl]-methanone According to the procedure described for the synthesis of 4-[6-(4-isopropyl-piperazine-1-carbonyl)-1H-indol-3-yl]-piperidine-1-carboxylic acid diethylamide (example 30) the title compound was prepared from (4-isopropyl-piperazin-1-yl)-(3-piperidin-4-yl-1H-indol-6-yl)-methanone; hydrochloride (example 7) and methanesulfonylchloride (commercially available). MS (m/e): 433.3 (MH$^+$).

Example 34

[1-Ethyl-3-(1-isobutyl-1,2,3,6-tetrahydro-pyridin-4-yl)-1H-indol-6-yl]-(4-isopropyl-piperazin-1-yl)-methanone; hydrochloride A mixture of 41 mg (0.1 mmol) [3-(1-isobutyl-1,2,3,6-tetrahydro-pyridin-4-yl)-1H-indol-6-yl]-(4-isopropyl-piperazin-1-yl)-methanone; hydrochloride (example 1), 12 mg (0.11 mmol) potassium tert-butoxide and 17 mg (0.11 mmol) iodoethane (commercially available) in 3 mL THF was stirred for 1 h at room temperature. Isolute was added and the mixture was evaporated to dryness. The residue was purified by flash column chromatography on silica eluting with a mixture formed from DCM, MeOH and NH$_3$ aq. to yield after evaporation of the combined product fractions and treatment with HCl in MeOH 48 mg (94%) of the title compound as yellow foam. MS (m/e): 437.3 (MH$^+$).

Example 35

(4-Cyclopentyl-piperazin-1-yl)-[3-(1-methyl-pyrrolidin-2-yl)-1H-indol-6-yl]-methanone a) Step 1: 3-[1-Methyl-pyrrolidin-(2Z)-ylidene]-3H-indole-6-carboxylic acid methyl ester A mixture of 1.6 mL (16 mmol) 1-methyl-2-pyrrolidone and 10 mL phosphoryl chloride (POCl$_3$) in 10 mL 1,2-dichloroethane was stirred for 15 min and 1.75 g (10 mmol) methyl indole-6-carboxylate and 1.6 mL (16 mmol) 1-methyl-2-pyrrolidone in 10 mL 1,2-dichloroethane was added. The mixture was heated to reflux for 2 h. Water and Na$_2$CO$_3$ aq. was added to adjust to pH=9. Subsequently the mixture was extracted with DCM and the combined organic layers were washed with water, dried with Na$_2$SO$_4$ and evaporated to dryness. Trituration with acetone provided 1.45 g (57%) of the title compound as light brown solid. MS (m/e): 257.2 (MH$^+$).

b) Step 2: 3-[1-Methyl-pyrrolidin-(2Z)-ylidene]-3H-indole-6-carboxylic acid; hydrochloride A mixture of 1.45 g (5.7 mmol) 3-[1-Methyl-pyrrolidin-(2Z)-ylidene]-3H-indole-6-carboxylic acid methyl ester and 0.38 g (9.1 mmol) LiOH.H$_2$O in 50 mL THF and 50 mL water was heated to reflux for 3 h. The organic volatiles were evaporated and 4N HCl aq. was added to adjust to pH=2. The precipitate was filtered off and in methanol/acetone suspended. The precipitate was filtered off washed with acetone and dried to provide 1.28 g (81%) of the title compound as light brown solid. MS (m/e): 243.3 (MH$^+$).

c) Step 3: (4-Cyclopentyl-piperazin-1-yl)-{3-[1-methyl-pyrrolidin-(2Z)-ylidene]-3H-indol-6-yl}-methanone A mixture of 0.4 g (1.43 mmol) 3-[1-Methyl-pyrrolidin-(2Z)-ylidene]-3H-indole-6-carboxylic acid; hydrochloride, 0.53 g (1.7 mmol) TBTU, 1.11 g (8.7 mmol) DIPEA and 0.27 g (1.73 mmol) 1-cyclopentyl-piperazine in 30 mL DMF was stirred at room temperature for 16 h. After evaporation of all volatiles acetone, THF and Na$_2$CO$_3$ (aq. 10%) was added and extracted with THF and acetone. The combined organic layers were washed with NaCl aq. sat., dried with Na$_2$SO$_4$ and evaporated to dryness. Isolute and DCM were added and again evaporated to dryness. The residue was purified by flash column chromatography on silica eluting with a mixture formed from DCM, MeOH and NH$_3$ aq. to yield after evaporation of the combined product fractions and subsequent crystallization from ethyl acetate and diethyl ether 209 mg (38%) of the title compound as white solid. MS (m/e): 379.3 (MH$^+$).

d) Step 4: (4-Cyclopentyl-piperazin-1-yl)-[3-(1-methyl-pyrrolidin-2-yl)-1H-indol-6-yl]-methanone A mixture of 50 mg (0.13 mmol) (4-cyclopentyl-piperazin-1-yl)-{3-[1-methyl-pyrrolidin-(2Z)-ylidene]-3H-indol-6-yl}-methanone and 15 mg (0.39 mmol) sodium borohydride in 4 mL ethanol was stirred at room temperature for 16 h. After evaporation of all volatiles 20 mL DCM 0.5 mL water and 0.5 mL 4N NaOH aq. was added and after 30 min treated with Na$_2$SO$_4$, filtered and evaporated to dryness. The residue was purified by flash column chromatography on silica eluting with a mixture formed from DCM, MeOH and NH$_3$ aq. to yield after evaporation of the combined product fractions 45 mg (90%) of the title compound as white foam. MS (m/e): 381.3 (MH$^+$).

Example 36

(4-Isopropyl-piperazin-1-yl)-[3-(1-methyl-pyrrolidin-2-yl)-1H-indol-6-yl]-methanone a) Step 1: (4-Isopropyl-piperazin-1-yl)-{3-[1-methyl-pyrrolidin-(2Z)-ylidene]-3H-indol-6-yl}-methanone According to the procedure described for the synthesis of (4-cyclopentyl-piperazin-1-yl)-{3-[1-methyl-pyrrolidin-(2Z)-ylidene]-3H-indol-6-yl}-methanone (example 35, step 3) the title compound was prepared from 3-[1-methyl-pyrrolidin-(2Z)-ylidene]-3H-indole-6-carboxylic acid; hydrochloride and cyclopentylpiperazine (commercially available). MS (m/e): 353.3 (MH$^+$).

b) Step 2: (4-Isopropyl-piperazin-1-yl)-[3-(1-methyl-pyrrolidin-2-yl)-1H-indol-6-yl]-methanone According to the procedure described for the synthesis of (4-cyclopentyl-piperazin-1-yl)-[3-(1-methyl-pyrrolidin-2-yl)-1H-indol-6-yl]-methanone (example 35, step 4) the title compound was prepared from (4-isopropyl-piperazin-1-yl)-

{3-[1-methyl-pyrrolidin-(2Z)-ylidene]-3H-indol-6-yl}-methanone through reduction with sodium borohydride. MS (m/e): 355.3 (MH+).

Example 37

[3-(1-Benzyl-pyrrolidin-2-yl)-1H-indol-6-yl]-(4-isopropyl-piperazin-1-yl)-methanone a) Step 1: 3-[1-Benzyl-pyrrolidin-(2Z)-ylidene]-3H-indole-6-carboxylic acid methyl ester According to the procedure described for the synthesis of 3-[1-Methyl-pyrrolidin-(2Z)-ylidene]-3H-indole-6-carboxylic acid methyl ester (example 35, step 1) the title compound was prepared from methyl indole-6-carboxylate (commercially available) and 1-benzyl-pyrrolidinone (commercially available). MS (m/e): 333.2 (MH+).

b) Step 2: 3-(1-Benzyl-pyrrolidin-2-yl)-1H-indole-6-carboxylic acid methyl ester According to the reduction procedure described for the synthesis of (4-cyclopentyl-piperazin-1-yl)-[3-(1-methyl-pyrrolidin-2-yl)-1H-indol-6-yl]-methanone (example 35, step 4) the title compound was prepared from 3-[1-benzyl-pyrrolidin-(2Z)-ylidene]-3H-indole-6-carboxylic acid methyl ester through reduction with sodium borohydride. MS (m/e): 335.3 (MH+).

c) Step 3: 3-(1-Benzyl-pyrrolidin-2-yl)-1H-indole-6-carboxylic acid, hydrochloride According to the procedure described for synthesis of 3-[1-methyl-pyrrolidin-(2Z)-ylidene]-3H-indole-6-carboxylic acid; hydrochloride (example 35, step 2) the title compound was prepared from 3-(1-benzyl-pyrrolidin-2-yl)-1H-indole-6-carboxylic acid methyl ester and LiOH.H2O. MS (m/e): 321.1 (MH+).

d) Step 4: [3-(1-Benzyl-pyrrolidin-2-yl)-1H-indol-6-yl]-(4-isopropyl-piperazin-1-yl)-methanone According to the procedure described for the synthesis of (4-cyclopentyl-piperazin-1-yl)-{3-[1-methyl-pyrrolidin-(2Z)-ylidene]-3H-indol-6-yl}-methanone (example 35, step 3) the title compound was prepared from 3-(1-benzyl-pyrrolidin-2-yl)-1H-indole-6-carboxylic acid, hydrochloride and 1-(2-propyl)-piperazine (commercially available). MS (m/e): 431.3 (MH+).

Example 38

[3-(1-Benzyl-pyrrolidin-2-yl)-1H-indol-6-yl]-(4-cyclopentyl-piperazin-1-yl)-methanone According to the procedure described for the synthesis of [3-(1-benzyl-pyrrolidin-2-yl)-1H-indol-6-yl]-(4-isopropyl-piperazin-1-yl)-methanone (example 37, step 4) the title compound was prepared from 3-(1-Benzyl-pyrrolidin-2-yl)-1H-indole-6-carboxylic acid, hydrochloride and cyclopentyl piperazine (commercially available). MS (m/e): 457.3 (MH+).

Example 39

(4-Isopropyl-piperazin-1-yl)-{3-[1-(4-methoxy-phenyl)-1,2,3,6-tetrahydro-pyridin-4-yl]-1H-indol-6-yl}-methanone a) Step 1: 3-[1-(4-Methoxy-phenyl)-1,2,3,6-tetrahydro-pyridin-4-yl]-1H-indole-6-carboxylic acid hydrochloride A mixture of 0.3 g (1.8 mmol) indole-6-carboxylic acid, 0.764 g (3.7 mmol) 1-(4-Methoxy-phenyl)-piperidin-4-one and 0.348 g (6.2 mmol) KOH pellets in 8 ml methanol was stirred at reflux for 24 h. The precipitate was filtered off, washed with methanol and diethyl ether and transferred into the respective hydrochloride salt ba treatment with 2N HCl in methanol. Filtration of the mixture, washing of the precipitate with diethyl ether and drying yielded 0.506 g (70%) of the title compound as red solid. MS (m/e): 349.2 (MH+).

b) Step 2: 4-Isopropyl-piperazin-1-yl)-{3-[1-(4-methoxy-phenyl)-1,2,3,6-tetrahydro-pyridin-4-yl]-1H-indol-6-yl}-methanone According to the coupling procedure described like for instance for (1H-indol-6-yl)-(4-isopropyl-piperazin-1-yl)-methanone (example 1, step 1) the title compound was prepared from 3-[1-(4-methoxy-phenyl)-1,2,3,6-tetrahydro-pyridin-4-yl]-1H-indole-6-carboxylic acid hydrochloride and 1-(2-propyl)-piperazine (commercially available). MS (m/e): 459.3 (MH+).

Example 40

(4-Isopropyl-piperazin-1-yl)-{3-[1-(4-methoxy-phenyl)-piperidin-4-yl]-1H-indol-6-yl}-methanone; hydrochloride According to the hydrogenation procedure like described for instance for [3-(1-isobutyl-piperidin-4-yl)-1H-indol-6-yl]-(4-isopropyl-piperazin-1-yl)-methanone; hydrochloride (example 2) the title compound was prepared from (4-isopropyl-piperazin-1-yl)-{3-[1-(4-methoxy-phenyl)-1,2,3,6-tetrahydro-pyridin-4-yl]-1H-indol-6-yl}-methanone in methanol/HCl. MS (m/e): 461.2 (MH+).

Example 41

(4-Cyclopentyl-piperazin-1-yl)-{3-[1-(4-methoxy-phenyl)-piperidin-4-yl]-1H-indol-6-yl}-methanone; hydrochloride a) Step 1: (4-Cyclopentyl-piperazin-1-yl)-{3-[1-(4-methoxy-phenyl)-1,2,3,6-tetrahydro-pyridin-4-yl]-1H-indol-6-yl}-methanone According to the coupling procedure described like for instance for (1H-indol-6-yl)-(4-isopropyl-piperazin-1-yl)-methanone (example 1, step 1) the title compound was prepared from 3-[1-(4-methoxy-phenyl)-1,2,3,6-tetrahydro-pyridin-4-yl]-1H-indole-6-carboxylic acid hydrochloride and cyclopentyl-piperazine (commercially available). MS (m/e): 485.5 (MH+).

b) Step 2: 4-Cyclopentyl-piperazin-1-yl)-{3-[1-(4-methoxy-phenyl)-piperidin-4-yl]-1H-indol-6-yl}-methanone; hydrochloride According to the hydrogenation procedure like described for instance for [3-(1-isobutyl-piperidin-4-yl)-1H-indol-6-yl]-(4-isopropyl-piperazin-1-yl)-methanone; hydrochloride (example 2) the title compound was prepared from (4-cyclopentyl-piperazin-1-yl)-{3-[1-(4-methoxy-phenyl)-1,2,3,6-tetrahydro-pyridin-4-yl]-1H-indol-6-yl}-methanone in methanol/HCl. MS (m/e): 487.4 (MH+).

Example 42

[3-(1-Isobutyl-1,2,3,6-tetrahydro-pyridin-4-yl)-1-methyl-1H-indol-6-yl]-(4-isopropyl-piperazin-1-yl)-methanone; hydrochloride A mixture of 41 mg (0.1 mmol) [3-(1-isobutyl-1,2,3,6-tetrahydro-pyridin-4-yl)-1H-indol-6-yl]-(4-isopropyl-piperazin-1-yl)-methanone (example 1, free base), 12 mg (0.1 mmol) potassium tert.-butoxide and 21.3 mg (0.15 mmol) iodomethane in 3 ml THF was reacted at room temperature over night. Isolute was added and the mixture was evaporated to dryness and subsequently purified by flash column chromatography eluting with a mixture formed from DCM, MeOH and NH$_3$ aq. to yield after evaporation of the combined product fractions and transforming the free base into the respective hydrochloride salt with methanol/HCl 43 mg (86%) of the title compound as yellow foam. MS (m/e): 423.1 (MH$^+$).

Example 43

[3-(1-Isobutyl-1,2,3,6-tetrahydro-pyridin-4-yl)-1-isopropyl-1H-indol-6-yl]-(4-isopropyl-piperazin-1-yl)-methanone; hydrochloride According to the procedure described for the synthesis of [3-(1-isobutyl-1,2,3,6-tetrahydro-pyridin-4-yl)-1-methyl-1H-indol-6-yl]-(4-isopropyl-piperazin-1-yl)-methanone; hydrochloride (example 42) the title compound was prepared from [3-(1-isobutyl-1,2,3,6-tetrahydro-pyridin-4-yl)-1H-indol-6-yl]-(4-isopropyl-piperazin-1-yl)-methanone and 2-iodopropane (commercially available). MS (m/e): 451.2 (MH$^+$).

Example 44

[3-(1-Isobutyl-1,2,3,6-tetrahydro-pyridin-4-yl)-1-methanesulfonyl-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-methyl-1H-indol-6-yl]-(4-isopropyl-piperazin-1-yl)-methanone; hydrochloride (example 42) the title compound was prepared from [3-(1-isobutyl-1,2,3,6-tetrahydro-pyridin-4-yl)-1H-indol-6-yl]-(4-isopropyl-piperazin-1-yl)-methanone and methanesulfonylchloride (commercially available). MS (m/e): 487.3 (MH$^+$).

Example 45

[3-(1-Isobutyl-piperidin-4-yl)-1-methyl-1H-indol-6-yl]-(4-isopropyl-piperazin-1-yl)-methanone; hydrochloride According to the procedure described for the synthesis of [3-(1-isobutyl-1,2,3,6-tetrahydro-pyridin-4-yl)-1-methyl-1H-indol-6-yl]-(4-isopropyl-piperazin-1-yl)-methanone; hydrochloride (example 42) the title compound was prepared from [3-(1-isobutyl-piperidin-4-yl)-1H-indol-6-yl]-(4-isopropyl-piperazin-1-yl)-methanone (example 2, free base) and iodomethane (commercially available). MS (m/e): 425.2 (MH$^+$).

Example 46

[1-Ethyl-3-(1-isobutyl-piperidin-4-yl)-1H-indol-6-yl]-(4-isopropyl-piperazin-1-yl)-methanone; hydrochloride According to the procedure described for the synthesis of [3-(1-isobutyl-1,2,3,6-tetrahydro-pyridin-4-yl)-1-methyl-1H-indol-6-yl]-(4-isopropyl-piperazin-1-yl)-methanone; hydrochloride (example 42) the title compound was prepared from [3-(1-isobutyl-piperidin-4-yl)-1H-indol-6-yl]-(4-isopropyl-piperazin-1-yl)-methanone (example 2, free base) and iodoethane (commercially available). MS (m/e): 439.3 (MH$^+$).

Example 47

[3-(1-Isobutyl-piperidin-4-yl)-1-isopropyl-1H-indol-6-yl]-(4-isopropyl-piperazin-1-yl)-methanone; hydrochloride According to the procedure described for the synthesis of [3-(1-isobutyl-1,2,3,6-tetrahydro-pyridin-4-yl)-1-methyl-1H-indol-6-yl]-(4-isopropyl-piperazin-1-yl)-methanone; hydrochloride (example 42) the title compound was prepared from [3-(1-isobutyl-piperidin-4-yl)-1H-indol-6-yl]-(4-isopropyl-piperazin-1-yl)-methanone (example 2, free base) and 2-iodopropane (commercially available). MS (m/e): 453.5 (MH$^+$).

Example 48

[1-(2,2-Difluoro-ethyl)-3-(1-isobutyl-piperidin-4-yl)-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-methyl-1H-indol-6-yl]-(4-isopropyl-piperazin-1-yl)-methanone; hydrochloride (example 42) the title compound was prepared from [3-(1-isobutyl-piperidin-4-yl)-1H-indol-6-yl]-(4-isopropyl-piperazin-1-yl)-methanone (example 2, free base) and 2-bromo-1,1-difluoroethane (commercially available). MS (m/e): 475.2 (MH$^+$).

Example 49

[1-Isobutyl-3-(1-isobutyl-piperidin-4-yl)-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-methyl-1H-indol-6-yl]-(4-isopropyl-piperazin-1-yl)-methanone; hydrochloride (example 42) the title compound was prepared from [3-(1-isobutyl-piperidin-4-yl)-1H-indol-6-yl]-(4-isopropyl-piperazin-1-yl)-methanone (example 2, free base) and 1-iodo-2-methylpropane (commercially available). MS (m/e): 467.5 (MH$^+$).

Example 50

[3-(1-isobutyl-piperidin-4-yl)-1-methanesulfonyl-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-methyl-1H-indol-6-yl]-(4-isopropyl-piperazin-1-yl)-methanone; hydrochloride (example 42) the title compound was prepared from [3-(1-isobutyl-piperidin-4-yl)-1H-indol-6-yl]-(4-isopropyl-piperazin-1-yl)-methanone (example 2, free base) and methanesulfonylchloride (commercially available). MS (m/e): 489.2 (MH$^+$).

Example 51

4-[3-(1-Isobutyl-1,2,3,6-tetrahydro-pyridin-4-yl)-6-(4-isopropyl-piperazine-1-carbonyl)-indol-1-yl]-benzonitrile A mixture of 0.36 g (0.88 mmol) [3-(1-isobutyl-1,2,3,6-tetrahydro-pyridin-4-yl)-1H-indol-6-yl]-(4-isopropyl-piperazin-1-yl)-methanone (example 1, free base), 0.168 g (0.92 mmol) copper(II) acetate, powdered molecular sieves 4A, 0.388 g (2.64 mmol) (4-cyanophenyl)boronic acid and 0.446 g (4.4 mmol) NEt₃ in 20 ml 1,2-dichloroethane was heated to 85° C. for 66 h. The mixture was evaporated to dryness and the residue was purified by flash column chromatography eluting with a mixture formed from DCM, MeOH and NH₃ aq. to yield after evaporation of the combined product fractions 0.024 g (5%) of the title compound as yellow foam. MS (m/e): 510.5 (MH$^+$).

Example 52

[3-(1-Isobutyl-1,2,3,6-tetrahydro-pyridin-4-yl)-1-(4-trifluoromethyl-phenyl)-1H-indol-6-yl]-(4-isopropyl-piperazin-1-yl)-methanone A mixture of 0.15 g (0.36 mmol) [3-(1-isobutyl-1,2,3,6-tetrahydro-pyridin-4-yl)-1H-indol-6-yl]-(4-isopropyl-piperazin-1-yl)-methanone, 0.11 mg (0.4 mmol) 4-iodobenzotrifluoride, 12 mg (0.1 mmol) trans-1-2-diaminocyclohexane, 5 mg (0.026 mmol) copper(I)iodide and 0.164 g (0.77 mmol) potassium phosphate in 1.5 mL dioxane was heated to 130° C. for 17 h. Isolute was added and the mixture was evaporated to dryness and purified by flash column chromatography on silica eluting with a mixture formed from DCM, MeOH and NH₃ aq. to yield after evaporation of the combined product fractions 0.127 g (59%) of the title compound as white foam. MS (m/e): 468.1/553.3 (MH$^+$).

Example 53

[3-(1-Isobutyl-1,2,3,6-tetrahydro-pyridin-4-yl)-1-(4-methoxy-phenyl)-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-1,2,3,6-tetrahydro-pyridin-4-yl)-1H-indol-6-yl]-(4-isopropyl-piperazin-1-yl)-methanone and 4-iodoanisole (commercially available). MS (m/e): 430.2/515.3 (MH$^+$).

Example 54

[1-(2,4-Difluoro-phenyl)-3-(1-isobutyl-1,2,3,6-tetrahydro-pyridin-4-yl)-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-1,2,3,6-tetrahydro-pyridin-4-yl)-1H-indol-6-yl]-(4-isopropyl-piperazin-1-yl)-methanone and 2,4-difluoro-iodobenzene (commercially available). MS (m/e): 436.2/521.3 (MH$^+$).

Example 55

[1-(4-Fluoro-phenyl)-3-(1-isobutyl-1,2,3,6-tetrahydro-pyridin-4-yl)-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-1,2,3,6-tetrahydro-pyridin-4-yl)-1H-indol-6-yl]-(4-isopropyl-piperazin-1-yl)-methanone and 4-fluoro-iodobenzene (commercially available). MS (m/e): 418.4/503.4 (MH$^+$).

Example 56

[3-(1-Isobutyl-1,2,3,6-tetrahydro-pyridin-4-yl)-1-pyridin-3-yl-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-1,2,3,6-tetrahydro-pyridin-4-yl)-1H-indol-6-yl]-(4-isopropyl-piperazin-1-yl)-methanone and 3-iodopyridine (commercially available). MS (m/e): 401.3/486.4 (MH$^+$).

Example 57

[1-(3-Chloro-4-methyl-phenyl)-3-(1-isobutyl-1,2,3,6-tetrahydro-pyridin-4-yl)-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-1,2,3,6-tetrahydro-pyridin-4-yl)-1H-indol-6-yl]-(4-isopropyl-piperazin-1-yl)-methanone and 2-chloro-4-iodotoluene (commercially available). MS (m/e): 448.3/533.3 (MH$^+$).

Example 58

[1-(5-Fluoro-2-methyl-phenyl)-3-(1-isobutyl-1,2,3,6-tetrahydro-pyridin-4-yl)-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-1,2,3,6-tetrahydro-pyridin-4-yl)-1H-indol-6-yl]-(4-isopropyl-piperazin-1-yl)-methanone and 4-fluoro-2-iodotoluene (commercially available). MS (m/e): 432.4/517.4 (MH$^+$).

Example 59

[3-(1-Isobutyl-1,2,3,6-tetrahydro-pyridin-4-yl)-1-p-tolyl-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-1,2,3,6-tetrahydro-pyridin-4-yl)-1H-indol-6-yl]-(4-isopropyl-piperazin-1-yl)-methanone and 4-iodotoluene (commercially available). MS (m/e): 414.4/499.5 (MH$^+$).

Example 60

3-[3-(1-Isobutyl-1,2,3,6-tetrahydro-pyridin-4-yl)-6-(4-isopropyl-piperazine-1-carbonyl)-indol-1-yl]-benzonitrile According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-1,2,3,6-tetrahydro-pyridin-4-yl)-1H-indol-6-yl]-(4-isopropyl-piperazin-1-yl)-methanone and 3-iodobenzonitrile (commercially available). MS (m/e): 425.1/510.5 (MH$^+$).

Example 61

[3-(1-Isobutyl-piperidin-4-yl)-1-(4-trifluoromethyl-phenyl)-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-piperidin-4-yl)-1H-indol-6-yl]-(4-isopropyl-piperazin-1-yl)-methanone and 4-iodobenzotrifluoride (commercially available). MS (m/e): 555.4 (MH$^+$).

Example 62

[3-(1-Isobutyl-piperidin-4-yl)-1-(4-methoxy-phenyl)-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-piperidin-4-yl)-1H-indol-6-yl]-(4-isopropyl-piperazin-1-yl)-methanone and 4-iodoanisole (commercially available). MS (m/e): 517.4 (MH$^+$).

Example 63

[1-(2,4-Difluoro-phenyl)-3-(1-isobutyl-piperidin-4-yl)-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-piperidin-4-yl)-1H-indol-6-yl]-(4-isopropyl-piperazin-1-yl)-methanone and 2,4-difluoro-iodobenzene (commercially available). MS (m/e): 523.6 (MH$^+$).

Example 64

4-[3-(1-Isobutyl-piperidin-4-yl)-6-(4-isopropyl-piperazine-1-carbonyl)-indol-1-yl]-benzonitrile According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-piperidin-4-yl)-1H-indol-6-yl]-(4-isopropyl-piperazin-1-yl)-methanone and 4-iodobenzonitrile (commercially available). MS (m/e): 512.5 (MH$^+$).

Example 65

[3-(1-Isobutyl-piperidin-4-yl)-1-(3-trifluoromethyl-phenyl)-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-piperidin-4-yl)-1H-indol-6-yl]-(4-isopropyl-piperazin-1-yl)-methanone and 3-iodobenzotrifluoride (commercially available). MS (m/e): 555.4 (MH$^+$).

Example 66

[1-(4-Fluoro-phenyl)-3-(1-isobutyl-piperidin-4-yl)-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-piperidin-4-yl)-1H-indol-6-yl]-(4-isopropyl-piperazin-1-yl)-methanone and 4-fluoro-iodobenzene (commercially available). MS (m/e): 505.4 (MH$^+$).

Example 67

[3-(1-Isobutyl-piperidin-4-yl)-1-pyridin-3-yl-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-piperidin-4-yl)-1H-indol-6-yl]-(4-isopropyl-piperazin-1-yl)-methanone and 3-iodppyridine (commercially available). MS (m/e): 488.5 (MH$^+$).

Example 68

[1-(3-Chloro-4-methyl-phenyl)-3-(1-isobutyl-piperidin-4-yl)-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-piperidin-4-yl)-1H-indol-6-yl]-(4-isopropyl-piperazin-1-yl)-methanone and 2-chloro-4-iodotoluene (commercially available). MS (m/e): 535.4 (MH$^+$).

Example 69

[3-(1-Isobutyl-piperidin-4-yl)-1-p-tolyl-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-piperidin-4-yl)-1H-indol-6-yl]-(4-isopropyl-piperazin-1-yl)-methanone and 4-iodotoluene (commercially available). MS (m/e): 501.4 (MH$^+$).

Example 70

3-[3-(1-Isobutyl-piperidin-4-yl)-6-(4-isopropyl-piperazine-1-carbonyl)-indol-1-yl]-benzonitrile According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-piperidin-4-yl)-1H-indol-6-yl]-(4-isopropyl-piperazin-1-yl)-methanone and 3-iodobenzonitrile (commercially available). MS (m/e): 512.5 (MH$^+$).

Example 71

[3-(1-Isobutyl-piperidin-4-yl)-1-(4-trifluoromethoxy-phenyl)-1H-indol-6-yl]-(4-isopropyl-piperazin-1-yl)-methanone According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from [3-(1-isobutyl-piperidin-4-yl)-1H-indol-6-yl]-(4-isopropyl-piperazin-1-yl)-methanone and 4-(trifluoromethoxy) iodobenzene (commercially available). MS (m/e): 571.3 (MH$^+$).

Example 72

(4-Isopropyl-piperazin-1-yl)-(3-piperidin-2-yl-1H-indol-6-yl)-methanone a) Step 1: 3-(1-Benzyl-piperidin-2-yl)-1H-indole-6-carboxylic acid methyl ester A mixture of 7.08 g (40 mmol) methyl indole-6-carboxylate, 12.5 g (66 mmol) 1-benzyl-2-piperidone and 8.16 g (53 mmol) POCl$_3$ in 60 mL 1,2-dichloroethane was heated to reflux for 2 h. The mixture was poured onto ice/water, adjusted to pH=9 with Na$_2$CO$_3$ aq (10%) and extracted with DCM. The combined organic phases were washed with NaCl aq. dried with Na$_2$SO$_4$ and evaporated to dryness. The residue was taken up with isolute and purified by column chromatography on silica eluting with a gradient formed from DCM/methanol/NH$_3$ aq. The product fractions were evaporated and used without further purification in the subsequent reaction by addition of 200 mL methanol and 3.37 g (89 mmol) sodium borohydride (NaBH$_4$) and stirring for 40 h at room temperature. After evaporation DCM, water and Na$_2$CO$_3$ aq. was added and the organic layer was washed with NaCl aq., dried with Na$_2$SO$_4$. and evaporated to dryness. The residue was taken up with isolute/DCM and after evaporation purified by column chromatography on silica eluting with a gradient formed from DCM/methanol/NH$_3$ aq. The product fractions were evaporated to yield 1.25 g (9%) of the title compound as light yellow solid. MS (m/e): 349.2 (MH$^+$).

b) Step 2: [3-(1-Benzyl-piperidin-2-yl)-1H-indol-6-yl]-(4-isopropyl-piperazin-1-yl)-methanone A mixture of 1.25 g (4 mmol) 3-(1-benzyl-piperidin-2-yl)-1H-indole-6-carboxylic acid methyl ester and 0.2 g (4.8 mmol) LiOH.H$_2$O in 40 mL water and 40 mL methanol was heated to reflux for 20 h. After 4 h additional 0.56 g LiOH.H$_2$O and 30 mL water was added. After evaporation of the methanol the mixture was adjusted to pH=2 and evaporated to dryness. 25 mL DMF was added and together with 1.4 g (4 mmol) TBTU, 2.8 g (22 mmol) DIPEA and 0.55 g (4 mmol) 1-(2-propyl)-piperazine stirred at room temperature for 3 h. Isolute was added and after evaporation purified by column chromatography on silica eluting with a gradient formed from DCM/methanol/NH$_3$ aq. The product fractions were evaporated to yield 1.14 g (71%) of the title compound as light brown solid. MS (m/e): 445.3 (MH$^+$).

c) Step 3: (4-Isopropyl-piperazin-1-yl)-(3-piperidin-2-yl-1H-indol-6-yl)-methanone A mixture of 1.05 g (2.3 mmol) [3-(1-benzyl-piperidin-2-yl)-1H-indol-6-yl]-(4-isopropyl-piperazin-1-yl)-methanone and 0.125 g Pd/C (10%) in 30 mL acetic acid was hydrogenated with H$_2$ at 60° C. during 16 h. Filtration of the catalyst and evaporation to dryness yielded a residue which was taken up in methanol and NH$_4$OH aq. (25%) and evaporated again to dryness. The residue was purified by column chromatography on silica eluting with a gradient formed from DCM/methanol/NH$_3$ aq. The product fractions were evaporated to yield 0.41 g (50%) of the title compound as light brown foam. MS (m/e): 355.4 (MH$^+$).

Example 73

(4-Isopropyl-piperazin-1-yl)-[3-(1-isopropyl-piperidin-2-yl)-1H-indol-6-yl]-methanone A mixture of 75 mg (0.21 mmol) (4-isopropyl-piperazin-1-yl)-(3-piperidin-2-yl-1H-indol-6-yl)-methanone, 0.18 g (1 mmol) 2-iodopropane and 0.0.44 g (0.32 mmol) K$_2$CO$_3$ in 3 mL THF was heated to reflux for 16 h. The mixture was filtered and evaporated to dryness and again 0.18 g (1 mmol) 2-iodopropane and 0.0.44 g (0.32 mmol) K$_2$CO$_3$ and together with 2 mL N,N-dimethylacetamide heated to 150° C. for 1 h. The mixture was evaporated to dryness and the residue was purified by column chromatography on silica eluting with a gradient formed from DCM/methanol/NH$_3$ aq. The product fractions were evaporated to yield 0.04 g (47%) of the title compound as light brown solid. MS (m/e): 397.1 (MH$^+$).

Example 74

[3-(1-Isobutyl-piperidin-2-yl)-1H-indol-6-yl]-(4-isopropyl-piperazin-1-yl)-methanone According to the procedure described for the synthesis of (4-Isopropyl-piperazin-1-yl)-[3-(1-isopropyl-piperidin-2-yl)-1H-indol-6-yl]-methanone (example 73) the title compound was prepared from (4-Isopropyl-piperazin-1-yl)-(3-piperidin-2-yl-1H-indol-6-yl)-methanone and 1-iodo-2-methylpropane (commercially available). MS (m/e): 411.3 (MH$^+$).

Example 75

4-[6-(4-Isopropyl-piperazine-1-carbonyl)-3-piperidin-3-yl-indol-1-yl]-benzonitrile According to the procedure described for the synthesis of [3-(1-isobutyl-1,2,3,6-tetrahydro-pyridin-4-yl)-1-(4-trifluoromethyl-phenyl)-1H-indol-6-yl]-(4-isopropyl-piperazin-1-yl)-methanone (example 52) the title compound was prepared from (4-isopropyl-piperazin-1-yl)-(3-piperidin-3-yl-1H-indol-6-yl)-methanone and 4-iodobenzonitrile (commercially available). MS (m/e): 456.1 (MH$^+$).

Example 76

4-{3-[6-(4-Isopropyl-piperazine-1-carbonyl)-1H-indol-3-yl]-piperidin-1-yl}-benzonitrile A mixture of 0.177 g (0.5 mmol) (4-isopropyl-piperazin-1-yl)-(3-piperidin-3-yl-1H-indol-6-yl)-methanone, 0.147 g (0.1 mmol) 4-cyanophenyl boronic acid, 9 mg copper (II) acetate and 0.5 g molecular sieves 4A in 5 mL THF was stirred at room temperature for 96 h. Isolute was added, the mixture evaporated the residue purified by column chromatography on silica eluting with a gradient formed from DCM/methanol/NH₃ aq. The product fractions were evaporated to yield 0.011 g (4%) of the title compound as off-white foam. MS (m/e): 456.3 (MH⁺).

Example 77

{3-[1-(3,5-Difluoro-benzoyl)-piperidin-3-yl]-1H-indol-6-yl}-(4-isopropyl-piperazin-1-yl)-methanone A mixture of 0.02 g (0.56 mmol) (4-isopropyl-piperazin-1-yl)-(3-piperidin-3-yl-1H-indol-6-yl)-methanone, 0.01 g (0.06 mmol) 3,5-difluorobenzoic acid, 0.02 g (0.06 mmol) TBTU and 0.044 g (0.3 mmol) DIPEA in 0.8 mL DMF was stirred at room temperature for 16 h. The mixture was subjected to preparative HPLC purification on reversed phase eluting with a gradient formed from acetonitrile/water/NEt₃. Evaporation of the product fractions yielded 16 mg (57%) of the title compounds as off-white foam. MS (m/e): 495.4 (MH⁺).

Example 78

(4-Isopropyl-piperazin-1-yl)-{3-[1-(thiophene-3-carbonyl)-piperidin-3-yl]-1H-indol-6-yl}-methanone According to the procedure described for the synthesis of {3-[1-(3,5-difluoro-benzoyl)-piperidin-3-yl]-1H-indol-6-yl}-(4-isopropyl-piperazin-1-yl)-methanone (example 77) the title compound was prepared from (4-isopropyl-piperazin-1-yl)-(3-piperidin-3-yl-1H-indol-6-yl)-methanone and thiophene carboxylic acid (commercially available). MS (m/e): 465.1 (MH⁺).

Example 79

3-{3-[6-(4-Isopropyl-piperazine-1-carbonyl)-1H-indol-3-yl]-piperidine-1-carbonyl}-benzonitrile According to the procedure described for the synthesis of {3-[1-(3,5-Difluoro-benzoyl)-piperidin-3-yl]-1H-indol-6-yl}-(4-isopropyl-piperazin-1-yl)-methanone (example 77) the title compound was prepared from (4-isopropyl-piperazin-1-yl)-(3-piperidin-3-yl-1H-indol-6-yl)-methanone and 3-cyanobenzoic acid (commercially available). MS (m/e): 484.5 (MH⁺).

Example 80

{3-[1-(5-Fluoro-2-methyl-benzoyl)-piperidin-3-yl]-1H-indol-6-yl}-(4-isopropyl-piperazin-1-yl)-methanone According to the procedure described for the synthesis of {3-[1-(3,5-difluoro-benzoyl)-piperidin-3-yl]-1H-indol-6-yl}-(4-isopropyl-piperazin-1-yl)-methanone (example 77) the title compound was prepared from (4-isopropyl-piperazin-1-yl)-(3-piperidin-3-yl-1H-indol-6-yl)-methanone and 5-fluoro-2-methylbenzoic acid (commercially available). MS (m/e): 491.4 (MH⁺).

Example 81

{3-[1-(3,4-Difluoro-benzoyl)-piperidin-3-yl]-1H-indol-6-yl}-(4-isopropyl-piperazin-1-yl)-methanone According to the procedure described for the synthesis of {3-[1-(3,5-difluoro-benzoyl)-piperidin-3-yl]-1H-indol-6-yl}-(4-isopropyl-piperazin-1-yl)-methanone (example 77) the title compound was prepared from (4-isopropyl-piperazin-1-yl)-(3-piperidin-3-yl-1H-indol-6-yl)-methanone and 3,4-difluorobenzoic acid (commercially available). MS (m/e): 495.4 (MH⁺).

Example 82

4-{3-[6-(4-Isopropyl-piperazine-1-carbonyl)-1H-indol-3-yl]-piperidine-1-carbonyl}-benzonitrile According to the procedure described for the synthesis of {3-[1-(3,5-difluoro-benzoyl)-piperidin-3-yl]-1H-indol-6-yl}-(4-isopropyl-piperazin-1-yl)-methanone (example 77) the title compound was prepared from (4-isopropyl-piperazin-1-yl)-(3-piperidin-3-yl-1H-indol-6-yl)-methanone and 4-cyanobenzoic acid (commercially available). MS (m/e): 484.5 (MH⁺).

Example 83

{3-[1-(3,4-Dichloro-benzoyl)-piperidin-3-yl]-1H-indol-6-yl}-(4-isopropyl-piperazin-1-yl)-methanone According to the procedure described for the synthesis of {3-[1-(3,5-difluoro-benzoyl)-piperidin-3-yl]-1H-indol-6-yl}-(4-isopropyl-piperazin-1-yl)-methanone (example 77) the title compound was prepared from (4-isopropyl-piperazin-1-yl)-(3-piperidin-3-yl-1H-indol-6-yl)-methanone and 3,4-dichlorobenzoic acid (commercially available). MS (m/e): 527.3 (MH⁺).

Example 84

(4-Isopropyl-piperazin-1-yl)-{3-[1-(pyridine-4-carbonyl)-piperidin-3-yl]-1H-indol-6-yl}-methanone According to the procedure described for the synthesis of {3-[1-(3,5-Difluoro-benzoyl)-piperidin-3-yl]-1H-indol-6-yl}-(4-isopropyl-piperazin-1-yl)-methanone (example 77) the title compound was prepared from (4-isopropyl-piperazin-1-yl)-(3-piperidin-3-yl-1H-indol-6-yl)-methanone and isonicotinic acid (commercially available). MS (m/e): 460.4 (MH⁺).

Example 85

{3-[1-(3,4-Dimethoxy-benzoyl)-piperidin-3-yl]-1H-indol-6-yl}-(4-isopropyl-piperazin-1-yl)-methanone According to the procedure described for the synthesis of {3-[1-(3,5-difluoro-benzoyl)-piperidin-3-yl]-1H-indol-6-yl}-(4-isopropyl-piperazin-1-yl)-methanone (example 77) the title compound was prepared from (4-isopropyl-piperazin-1-yl)-(3-piperidin-3-yl-1H-indol-6-yl)-methanone and 3,4-dimethoxybenzoic acid (commercially available). MS (m/e): 519.3 (MH⁺).

Example 86

(4-Isopropyl-piperazin-1-yl)-{3-[1-(pyridine-3-carbonyl)-piperidin-3-yl]-1H-indol-6-yl}-methanone According to the procedure described for the synthesis of {3-[1-(3,5-difluoro-benzoyl)-piperidin-3-yl]-1H-indol-6-yl}-(4-isopropyl-piperazin-1-yl)-methanone (example 77) the title compound was prepared from (4-isopropyl-piper-

Example 87

(4-Isopropyl-piperazin-1-yl)-{3-[1-(4-trifluoromethoxy-benzoyl)-piperidin-3-yl]-1H-indol-6-yl}-methanone According to the procedure described for the synthesis of {3-[1-(3,5-difluoro-benzoyl)-piperidin-3-yl]-1H-indol-6-yl}-(4-isopropyl-piperazin-1-yl)-methanone (example 77) the title compound was prepared from (4-isopropyl-piperazin-1-yl)-(3-piperidin-3-yl-1H-indol-6-yl)-methanone and 4-trifluoromethoxybenzoic acid (commercially available). MS (m/e): 543.3 (MH$^+$).

Example 88

3-{3-[6-(4-Isopropyl-piperazine-1-carbonyl)-1H-indol-3-yl]-piperidin-1-yl}-benzonitrile According to the procedure described for the synthesis of 4-{3-[6-(4-isopropyl-piperazine-1-carbonyl)-1H-indol-3-yl]-piperidin-1-yl}-benzonitrile (example 76) the title compound was prepared from (4-isopropyl-piperazin-1-yl)-(3-piperidin-3-yl-1H-indol-6-yl)-methanone and 3-cyanophenyl boronic acid (commercially available). MS (m/e): 456.4 (MH$^+$).

Example 89

(4-Isopropyl-piperazin-1-yl)-{3-[1-(3-methoxy-phenyl)-piperidin-3-yl]-1H-indol-6-yl}-methanone According to the procedure described for the synthesis of 4-{3-[6-(4-isopropyl-piperazine-1-carbonyl)-1H-indol-3-yl]-piperidin-1-yl}-benzonitrile (example 76) the title compound was prepared from (4-isopropyl-piperazin-1-yl)-(3-piperidin-3-yl-1H-indol-6-yl)-methanone and 3-methoxyphenyl boronic acid (commercially available). MS (m/e): 461.4 (MH$^+$).

Example 90

[3-(4-Isobutyl-morpholin-2-yl)-1H-indol-6-yl]-(4-isopropyl-piperazin-1-yl)-methanone a) Step 1: 3-(2-Chloro-acetyl)-1H-indole-6-carboxylic acid methyl ester A mixture of 14 g (80 mmol) methyl indole-6-carboxylate, 40 mL (84 mmol) ethylmagnesium chloride (2M) in diethyl ether, 240 mL (240 mmol) zinc chloride (1M) in diethyl ether, 9.5 g (84 mmol) chloroacetyl chloride in 680 mL DCM was stirred at room temperature for 19 h. THF was added and diethyl ether and DCM were removed by evaporation. The mixture was treated with NH$_4$Cl aq. and ethyl acetate. The aqueous phase was extracted with THF/ethyl acetate and the combined organic layers were washed with NaCl aq., dried with Na$_2$SO$_4$ and evaporated. The residue was washed with ethyl acetate and dried under vacuum at 50° C. to yield 4 g (20%) of the title compound as light yellow solid. MS (m/e): 250.1 (M–H).

b) Step 2: 3-[2-(2-Hydroxy-ethylamino)-acetyl]-1H-indole-6-carboxylic acid methyl ester A mixture of 0.285 g (1.1 mmol) 3-(2-chloro-acetyl)-1H-indole-6-carboxylic acid methyl ester, 0.173 g (2.8 mmol) ethanolamine in 5 mL DMF was stirred at room temperature for 5 h. After evaporation of all volatiles the residue was taken up in DCM/methanol and isolute was added and after evaporation purified by column chromatography on silica eluting with a gradient formed from DCM/methanol/NH$_3$ aq. The product fractions were evaporated to yield after crystallization from methanol/diethyl ether 0.13 g (41%) of the title compound as off-white solid. MS (m/e): 277.2 (MH$^+$).

c) Step 3: 3-Morpholin-2-yl-1H-indole-6-carboxylic acid methyl ester

A mixture of 1.8 g (6.5 mmol) 3-[2-(2-Hydroxy-ethylamino)-acetyl]-1H-indole-6-carboxylic acid methyl ester and 4.2 g (111 mmol) sodium borohydride in 700 mL methanol was stirred at room temperature for 20 h. After evaporation the residue was treated with THF, ethyl acetate and Na$_2$CO$_3$ aq. (10%) and the aqueous phase extracted with THF/ethyl acetate. The combined organic layers were washed with NaCl aq., dried with Na$_2$SO$_4$ and evaporated to dryness. The residue was taken up in 50 mL methanol and treated at 0° C. with 32 mL 1.25 N HCl in methanol for 45 min. The mixture was evaporated to dryness and treated with THF, ethyl acetate and Na$_2$CO$_3$ aq. (10%) and the aqueous phase extracted with THF/ethyl acetate. The combined organic layers were washed with NaCl aq., dried with Na$_2$SO$_4$ and evaporated to dryness. The residue was taken up in DCM/methanol, isolute was added and after evaporation purified by column chromatography on silica eluting with a gradient formed from DCM/methanol/NH$_3$ aq. The product fractions were evaporated to yield 1.05 g (62%) of the title compound as light brown solid. MS (m/e): 261.2 (MH$^+$).

d) Step 4: 3-(4-Isobutyl-morpholin-2-yl)-1H-indole-6-carboxylic acid methyl ester A mixture of 500 mg (1.9 mmol) 3-Morpholin-2-yl-1H-indole-6-carboxylic acid methyl ester, 1.06 g (5.7 mmol) 1-iodo-2-methylpropane and 0.372 g (2.87 mmol) DIPEA in 30 mL dioxane was heated to reflux for 16 h. After filtration of the suspension the filtrate was evaporated to dryness and the residue dissolved in DCM and purified by column chromatography on silica eluting with a solvent mixture formed from DCM/methanol/NH$_3$ aq. The product fractions were evaporated to yield 0.59 g (97%) of the title compound as viscous yellow oil. MS (m/e): 317.4 (MH$^+$).

e) Step 5: [3-(4-Isobutyl-morpholin-2-yl)-1H-indol-6-yl]-(4-isopropyl-piperazin-1-yl)-methanone According to the procedure described for the conversion of an ester functionality to a piperazine amide functionality like in example 72, step 2 the title compound was prepared from 3-(4-isobutyl-morpholin-2-yl)-1H-indole-6-carboxylic acid methyl ester and (after ester cleavage with LiOH.H$_2$O), 1-(2-propyl)-piperazine (commercially available). The title compound was obtained as light brown foam. MS (m/e): 413.4 (MH$^+$).

Example 91

[3-(4-Isopropyl-morpholin-2-yl)-1H-indol-6-yl]-(4-isopropyl-piperazin-1-yl)-methanone According to the procedure described for the synthesis of [3-(4-isobutyl-morpholin-2-yl)-1H-indol-6-yl]-(4-isopropyl-piperazin-1-yl)-methanone (example 90) the title compounds was synthesized in consecutive steps from 3-morpholin-2-yl-1H-indole-6-carboxylic acid methyl ester and 2-iodopropane (commercially available) leading to 3-(4-isopropyl-morpholin-2-yl)-1H-indole-6-carboxylic acid methyl ester (MS (m/e): 303.4 (MH$^+$)) which was converted to the title compounds according to the procedure described for the conversion of an ester functionality to a piperazine amide functionality like in example 72, step 2. The title compound was prepared from 3-(4-isopropyl-morpholin-2-yl)-1H-indole-6-carboxylic acid methyl ester and (after ester cleavage with LiOH.H₂O), 1-(2-propyl)-piperazine (commercially available). The title compound was obtained as light yellow foam. MS (m/e): 399.3 (MH⁺).

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the previously mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| | |
| --- | --- |
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
| --- | --- |
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Unless stated to the contrary, all compounds in the examples were prepared and characterized as described. All ranges recited herein encompass all combinations and sub-combinations included within that range limit. All patents and publications cited herein are hereby incorporated by reference in their entirety.

The invention claimed is:
1. A compound of the formula

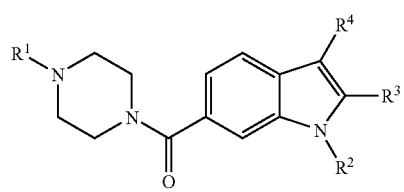

or a pharmaceutically acceptable salt thereof, wherein:
(a) $R^1$ is isopropyl or tert-butyl;
(b) $R^2$ is selected from the group consisting of:

(1) hydrogen;
(2) lower alkyl;
(3) lower halogenalkyl;
(4) —$SO_2$—$R^5$, wherein $R^5$ is lower alkyl or phenyl optionally substituted by one or two substituents independently selected from the group consisting of lower alkyl, lower alkoxy, halogen, cyano, lower halogenalkyl and lower halogenalkoxy;
(5) —C(O)—$(CH_2)_n$-phenyl, wherein n is 0, 1 or 2 and wherein the phenyl ring is optionally substituted by one or two substituents independently selected from the group consisting of lower alkyl, lower alkoxy, halogen, cyano, lower halogenalkyl and lower halogenalkoxy;
(6) —$(CH_2)_n$-cycloalkyl, wherein n is 0, 1 or 2;
(7) pyridyl; and
(8) —$(CH_2)_n$-phenyl, wherein n is 0, 1 or 2 and wherein the phenyl ring is optionally substituted by one, two or three substituents independently selected from the group consisting of lower alkyl, lower halogenalkyl, halogen, cyano, lower alkoxy and lower halogenalkoxy;
(c) $R^3$ is hydrogen or lower alkyl; and
(d) $R^4$ is an N-heterocyclic ring selected from the group consisting of pyrrolidine, piperidine, 1,2,3,6-tetrahydropyridine, and morpholine; wherein the nitrogen atom of the N-heterocyclic ring is substituted by a group selected from the group consisting of:
(1) hydrogen;
(2) lower alkyl;
(3) cycloalkyl;
(4) lower cyanoalkyl;
(5) lower halogenalkyl;
(6) lower alkoxyalkyl;
(7) —$SO_2$—$R^6$, wherein $R^6$ is selected from the group consisting of:
(i) lower alkyl,
(ii) phenyl which is optionally substituted by one or two substituents selected from the group consisting of lower alkyl, lower alkoxy, halogen, cyano, lower halogenalkyl and lower halogenalkoxy,
(iii) thienyl, and
(iv) pyridyl;
(8) —C(O)—$R^7$, wherein $R^7$ is selected from the group consisting of:
(i) lower alkyl,
(ii) phenyl which is optionally substituted by one or two substituents selected from the group consisting of lower alkyl, lower alkoxy, halogen, cyano, lower halogenalkyl and lower halogenalkoxy,
(iii) thienyl, and
(iv) pyridyl;
(9) —C(O)—$NR^8R^9$, wherein $R^8$ and $R^9$ independently from each other are selected from the group consisting of:
(i) lower alkyl,
(ii) phenyl, and
(iii) lower phenylalkyl;
or alternatively, $R^8$ and $R^9$ together with the nitrogen atom to which they are attached to, form a heterocyclic ring selected from the group consisting of pyrrolidine, piperidine, piperazine and morpholine, and
(10) —$(CH_2)_p$-phenyl, wherein p is 0, 1 or 2 and wherein the phenyl ring is optionally substituted by one or two substituents selected from the group consisting of lower alkyl, lower alkoxy, halogen, cyano, lower halogenalkyl and lower halogenalkoxy.

2. A compound of the formula:

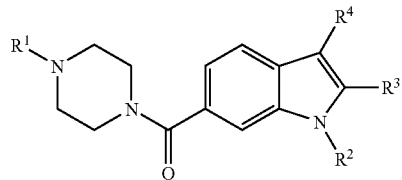

or a pharmaceutically acceptable salt thereof, wherein:
(a) $R^1$ is lower alkyl or cycloalkyl;
(b) $R^2$ is selected from the group consisting of:
(1) hydrogen;
(2) lower alkyl;
(3) lower halogenalkyl;
(4) —$SO_2$—$R^5$, wherein $R^5$ is lower alkyl or phenyl optionally substituted by one or two substituents independently selected from the group consisting of lower alkyl, lower alkoxy, halogen, cya no, lower halogenalkyl and lower halogenalkoxy;
(5) —C(O)—$(CH_2)_n$-phenyl, wherein n is 0, 1 or 2 and wherein the phenyl ring is optionally substituted by one or two substituents independently selected from the group consisting of lower alkyl, lower alkoxy, halogen, cyano, lower halogenalkyl and lower halogenalkoxy;
(6) —$(CH_2)_n$-cycloalkyl, wherein n is 0, 1 or 2;
(7) pyridyl; and
(8) —$(CH_2)_n$-phenyl, wherein n is 0, 1 or 2 and wherein the phenyl ring is optionally substituted by one, two or three substituents independently selected from the group consisting of lower alkyl, lower halogenalkyl, halogen, cyano, lower alkoxy and lower halogenalkoxy;
(c) $R^3$ is hydrogen or lower alkyl; and
(d) $R^4$ is pyrrolidine or morpholine; wherein the nitrogen atom of the pyrrolidine or morpholine ring is substituted by a substituent selected from the group consisting of:
(1) hydrogen;
(2) lower alkyl;
(3) cycloalkyl;
(4) lower cyanoalkyl;
(5) lower halogenalkyl;
(6) lower alkoxyalkyl;
(7) —$SO_2$—$R^6$, wherein $R^6$ is selected from the group consisting of:
(i) lower alkyl,
(ii) phenyl which is optionally substituted by one or two substituents selected from the group consisting of lower alkyl, lower alkoxy, halogen, cyano, lower halogenalkyl and lower halogenalkoxy,
(iii) thienyl, and
(iv) pyridyl;
(8) —C(O)—$R^7$, wherein $R^7$ is selected from the group consisting of:
(i) lower alkyl,
(ii) phenyl which is optionally substituted by one or two substituents selected from the group consisting of lower alkyl, lower alkoxy, halogen, cyano, lower halogenalkyl and lower halogenalkoxy,
(iii) thienyl, and
(iv) pyridyl;

(9) —C(O)—NR$^8$R$^9$, wherein R$^8$ and R$^9$ independently from each other are selected from the group consisting of:
  (i) lower alkyl,
  (ii) phenyl, and
  (iii) lower phenylalkyl;
or alternatively, R$^8$ and R$^9$ together with the nitrogen atom to which they are attached to, form a heterocyclic ring selected from the group consisting of pyrrolidine, piperidine, piperazine and morpholine, and
(10) —(CH$_2$)$_p$-phenyl, wherein p is 0,1 or 2 and wherein the phenyl ring is optionally substituted by one or two substituents selected from the group consisting of lower alkyl, lower alkoxy, halogen, cyano, lower halogenalkyl and lower halogenalkoxy.

3. A compound of the formula:

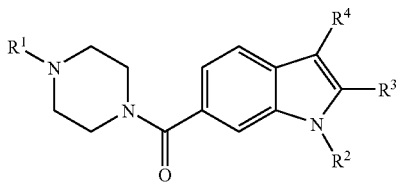

or a pharmaceutically acceptable salt thereof, wherein:
(a) R$^1$ is lower alkyl or cycloalkyl;
(b) R$^2$ is selected from the group consisting of:
  (1) hydrogen;
  (2) lower alkyl;
  (3) lower halogenalkyl;
  (4) —SO$_2$—R$^5$, wherein R$^5$ is lower alkyl or phenyl optionally substituted by one or two substituents independently selected from the group consisting of lower alkyl, lower alkoxy, halogen, cyano, lower halogenalkyl and lower halogenalkoxy;
  (5) —C(O)—(CH$_2$)$_n$-phenyl, wherein n is 0, 1 or 2 and wherein the phenyl ring is optionally substituted by one or two substituents independently selected from the group consisting of lower alkyl, lower alkoxy, halogen, cyano, lower halogenalkyl and lower halogenalkoxy;
  (6) —(CH$_2$)$_n$-cycloalkyl, wherein n is 0, 1 or 2;
  (7) pyridyl; and
  (8) —(CH$_2$)$_n$-phenyl, wherein n is 0, 1 or 2 and wherein the phenyl ring is optionally substituted by one, two or three substituents independently selected from the group consisting of lower alkyl, lower halogenalkyl, halogen, cyano, lower alkoxy and lower halogenalkoxy;
(c) R$^3$ is hydrogen or lower alkyl; and
(d) R$^4$ is an N-heterocyclic ring selected from the group consisting of pyrrolidine, piperidine, 1,2,3,6-tetrahydropyridine, and morpholine; wherein the nitrogen atom of the N-heterocyclic ring is substituted by a substituent selected from the group consisting of:
  (1) —SO$_2$—R$^6$, wherein R$^6$ is selected from the group consisting of:
    (i) lower alkyl,
    (ii) phenyl which is optionally substituted by one or two substituents selected from the group consisting of lower alkyl, lower alkoxy, halogen, cyano, lower halogenalkyl and lower halogenalkoxy,
    (iii) thienyl, and
    (iv) pyridyl;
  (2) —C(O)—R$^7$, wherein R$^7$ is selected from the group consisting of:
    (i) lower alkyl,
    (ii) phenyl which is optionally substituted by one or two substituents selected from the group consisting of lower alkyl, lower alkoxy, halogen, cyano, lower halogenalkyl and lower halogenalkoxy,
    (iii) thienyl, and
    (iv) pyridyl;
  (3) —C(O)—NR$^8$R$^9$, wherein R$^8$ and R$^9$ independently from each other are selected from the group consisting of:
    (i) lower alkyl,
    (ii) phenyl, and
    (iii) lower phenylalkyl;
  or alternatively, R$^8$ and R$^9$ together with the nitrogen atom to which they are attached to, form a heterocyclic ring selected from the group consisting of pyrrolidine, piperidine, piperazine and morpholine, and
  (4) —(CH$_2$)$_p$-phenyl, wherein p is 0, 1 or 2 and wherein the phenyl ring is optionally substituted by one or two substituents selected from the group consisting of lower alkyl, lower alkoxy, halogen, cyano, lower halogenalkyl and lower halogenalkoxy.

4. A compound of the formula:

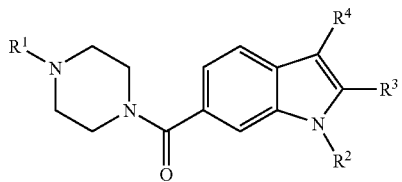

or a pharmaceutically acceptable salt thereof, wherein:
(a) R$^1$ is lower alkyl or cycloalkyl;
(b) R$^2$ is —(CH$_2$)$_n$-phenyl, wherein n is 0, 1 or 2 and wherein the phenyl ring is optionally substituted by one, two or three substituents independently selected from the group consisting of lower alkyl, lower halogenalkyl, halogen, cyano, lower alkoxy and lower halogenalkoxy;
(c) R$^3$ is hydrogen or lower alkyl; and
(d) R$^4$ is an N-heterocyclic ring selected from the group consisting of pyrrolidine, piperidine, 1,2,3,6-tetrahydropyridine, and morpholine; wherein the nitrogen atom of the N-heterocyclic ring is substituted by a substituent selected from the group consisting of:
  (1) hydrogen;
  (2) lower alkyl;
  (3) cycloalkyl;
  (4) lower cyanoalkyl;
  (5) lower halogenalkyl;
  (6) lower alkoxyalkyl;
  (7) —SO$_2$—R$^6$, wherein R6 is selected from the group consisting of:
    (i) lower alkyl,
    (ii) phenyl which is optionally substituted by one or two substituents selected from the group consisting of lower alkyl, lower alkoxy, halogen, cyano, lower halogenalkyl and lower halogenalkoxy,
    (iii) thienyl, and
    (iv) pyridyl;
  (8) —C(O)—R$^7$, wherein R$^7$ is selected from the group consisting of:

(i) lower alkyl,
(ii) phenyl which is optionally substituted by one or two substituents selected from the group consisting of lower alkyl, lower alkoxy, halogen, cyano, lower halogenalkyl and lower halogenalkoxy,
(iii) thienyl, and
(iv) pyridyl;
(9) —C(O)—NR$^8$R$^9$, wherein R$^8$ and R$^9$ independently from each other are selected from the group consisting of:
(i) lower alkyl,
(ii) phenyl, and
(iii) lower phenylalkyl;
or alternatively, R8 and R9 together with the nitrogen atom to which they are attached to, form a heterocyclic ring selected from the group consisting of pyrrolidine, piperidine, piperazine and morpholine, and
(10) —(CH$_2$)$_p$-phenyl, wherein p is 0,1 or 2 and wherein the phenyl ring is optionally substituted by one or two substituents selected from the group consisting of lower alkyl, lower alkoxy, halogen, cyano, lower halogenalkyl and lower halogenalkoxy.

5. A compound of claim 1 wherein the nitrogen atom of the N-heterocyclic ring of R$^4$ is substituted by a substituent selected from the group consisting of hydrogen, lower alkyl, cycloalkyl, lower cyanoalkyl, lower halogenalkyl, and lower alkoxyalkyl.

6. A compound of claim 1 wherein R$^4$ is piperidine or 1,2,3,6-tetrahydropyridine.

7. A compound of claim 1 wherein R$^2$ is hydrogen, lower alkyl, or lower halogenalkyl.

8. A compound of claim 1 wherein R$^2$ is selected from the group consisting of:
(1) —SO$_2$—R$^5$, wherein R$^5$ is lower alkyl or phenyl optionally substituted by one or two substituents independently selected from the group consisting of lower alkyl, lower alkoxy, halogen, cyano, lower halogenalkyl and lower halogenalkoxy;
(2) —C(O)—(CH$_2$)$_n$-phenyl, wherein n is 0, 1 or 2 and wherein the phenyl ring is optionally substituted by one or two substituents independently selected from the group consisting of lower alkyl, lower alkoxy, halogen, cyano, lower halogenalkyl and lower halogenalkoxy;
(3) —(CH$_2$)$_n$-cycloalkyl, wherein n is 0, 1 or 2;
(4) pyridyl; and
(5) —(CH$_2$)$_n$-phenyl, wherein n is 0, 1 or 2 and wherein the phenyl ring is optionally substituted by one, two or three substituents independently selected from the group consisting of lower alkyl, lower halogenalkyl, halogen, cyano, lower alkoxy and lower halogenalkoxy.

9. A compound of claim 1 wherein R$^3$ is hydrogen.

10. A compound of claim 3 wherein R$^1$ is lower alkyl.

11. A compound of claim 4 wherein n is 0.

12. A compound of claim 1 selected from the group consisting of:
[3-(1-isobutyl-piperidin-4-yl)-1H-indol-6-yl]-(4-isopropyl-piperazin-1-yl)-methanone,
(4-isopropyl-piperazin-1-yl)-[3-(1-isopropyl-piperidin-4-yl)-1H-indol-6-yl]-methanone,
and a pharmaceutically acceptable salt thereof.

13. A compound of claim 1, selected from the group consisting of:
[3-(1-cyclopentyl-piperidin-4-yl)-1H-indol-6-yl]-(4-isopropyl-piperazin-1-yl)-methanone,
[3-(1-isobutyl-1,2,3,6-tetrahydro-pyridin-4-yl)-1-isopropyl-1H-indol-6-yl]-(4-isopropyl-piperazin-1-yl)-methanone,
[1-(2,4-difluoro-phenyl)-3-(1-isobutyl-1,2,3,6-tetrahydro-pyridin-4-yl)-1H-indol-6-yl]-(4-isopropyl-piperazin-1-yl)-methanone,
and a pharmaceutically acceptable salt thereof.

14. A compound of claim 1, selected from the group consisting of:
[1-(2,4-difluoro-phenyl)-3-(1-isobutyl-piperidin-4-yl)-1H-indol-6-yl]-(4-isopropyl -piperazin-1-yl)-methanone,
[3-(1-isobutyl-piperidin-4-yl)-1-(3-trifluoromethyl-phenyl)-1H-indol-6-yl]-(4-isopropyl-piperazin-1-yl)-methanone,
3-[3-(1-isobutyl-piperidin-4-yl)-6-(4-isopropyl-piperazine-1-carbonyl)-indol-1-yl]-benzonitrile,
and a pharmaceutically acceptable salt thereof.

15. A compound of claim 1, selected from the group consisting of:
(4-isopropyl-piperazin-1-yl)-(3-piperidin-2-yl-1H-indol-6-yl)-methanone,
(4-isopropyl-piperazin-1-yl)-(3-morpholin-4-ylmethyl-1H-indol-6-yl)-methanone,
and a pharmaceutically acceptable salt thereof.

16. A compound which is (4-cyclopentyl-piperazin-1-yl)-[3-(1-isopropyl-piperidin -4-yl)-1 H-indol-6-yl]-methanone or a pharmaceutically acceptable salt thereof.

17. A pharmaceutical composition comprising a therapeutically effective amount of a compound of claim 1 and a pharmaceutically acceptable carrier and/or adjuvant.

* * * * *

UNITED STATES PATENT AND TRADEMARK OFFICE
CERTIFICATE OF CORRECTION

| | | |
|---|---|---|
| PATENT NO. | : 7,514,433 B2 | Page 1 of 1 |
| APPLICATION NO. | : 11/880083 | |
| DATED | : April 7, 2009 | |
| INVENTOR(S) | : Matthias Nettekoven and Olivier Roche | |

It is certified that error appears in the above-identified patent and that said Letters Patent is hereby corrected as shown below:

Column 53, Claim 1, line 27, delete "group" and insert -- substituent --.

Column 56, Claim 4, line 56, "R6" should be -- $R^6$ --.

Signed and Sealed this

Nineteenth Day of May, 2009

JOHN DOLL
*Acting Director of the United States Patent and Trademark Office*